US012285581B2

(12) United States Patent
Mathai et al.

(10) Patent No.: US 12,285,581 B2
(45) Date of Patent: *Apr. 29, 2025

(54) DRUG DELIVERY DEVICE AND METHODS FOR USING SAME

(71) Applicant: Pocket Naloxone Corp., Bethesda, MD (US)

(72) Inventors: Ashanthi Mathai, Bethesda, MD (US); Michael Frost, Warrington, PA (US); Serena Kim, Princeton, NJ (US); Franciscus Koppenhagen, Salem, NH (US); Seth Oringher, Rockville, MD (US)

(73) Assignee: Pocket Naloxone Corp., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/660,859

(22) Filed: May 10, 2024

(65) Prior Publication Data

US 2024/0293650 A1  Sep. 5, 2024

Related U.S. Application Data

(63) Continuation of application No. 17/682,261, filed on Feb. 28, 2022, now Pat. No. 12,017,026, which is a
(Continued)

(51) Int. Cl.
*A61M 31/00* (2006.01)
*A61K 9/00* (2006.01)
*A61K 31/485* (2006.01)

(52) U.S. Cl.
CPC .......... *A61M 31/00* (2013.01); *A61K 9/0043* (2013.01); *A61K 31/485* (2013.01); *A61M 2210/0618* (2013.01)

(58) Field of Classification Search
CPC .......... A61M 31/00; A61M 2210/0618; A61K 9/0043; A61K 31/485
See application file for complete search history.

(56) References Cited

U.S. PATENT DOCUMENTS 4,229,447 A  10/1980  Porter
4,464,378 A  10/1984  Hussain
(Continued)

FOREIGN PATENT DOCUMENTS

CA    2 795 156 A1  10/2011
CN    201 085 740     7/2008
(Continued)

OTHER PUBLICATIONS

Keller, et al., "Intranasal drug delivery: opportunities and toxicologic challenges during drug development", Drug Delivery and Translational Research, Jan. 25, 2021, vol. 12, No. 4, pp. 735-757.
(Continued)

*Primary Examiner* — Jessica Arble

(57) ABSTRACT

Devices for intranasal administration of naloxone are disclosed. The devices comprise a foam applicator and are configured to locate an applicator comprising a naloxone composition, in proximity to the middle turbinate and/or inferior turbinate. Naloxone can be delivered to the nasal mucosa by squeezing the nostril against the applicator. The device and methods of using the devices can be used to treat an opioid overdose.

14 Claims, 12 Drawing Sheets

Related U.S. Application Data continuation of application No. 17/463,079, filed on Aug. 31, 2021, now Pat. No. 11,278,709.

(60) Provisional application No. 63/177,772, filed on Apr. 21, 2021, provisional application No. 63/160,563, filed on Mar. 12, 2021.

(56) References Cited

U.S. PATENT DOCUMENTS

| | | |
|---|---|---|
| 4,476,116 A | 10/1984 | Anik |
| 4,596,795 A | 6/1986 | Pitha |
| 4,755,386 A | 7/1988 | Hsiao et al. |
| 4,938,763 A | 7/1990 | Dunn et al. |
| 5,011,692 A | 4/1991 | Fujioka et al. |
| 5,017,381 A | 5/1991 | Maruyama et al. |
| 5,116,817 A | 5/1992 | Anik |
| 5,229,135 A | 7/1993 | Philippon et al. |
| 5,324,519 A | 6/1994 | Dunn et al. |
| 5,562,077 A | 10/1996 | Schultz |
| 5,702,716 A | 12/1997 | Dunn et al. |
| 5,739,136 A | 4/1998 | Ellinwood et al. |
| 5,744,153 A | 4/1998 | Yewey et al. |
| 5,837,284 A | 11/1998 | Mehta et al. |
| 5,840,329 A | 11/1998 | Bai |
| 5,843,060 A | 12/1998 | Cercone |
| 5,866,154 A | 2/1999 | Bahal |
| 5,871,461 A | 2/1999 | Atanasoska |
| 5,990,194 A | 11/1999 | Dunn et al. |
| 6,391,452 B1 | 5/2002 | Antonsen et al. |
| 7,115,275 B2 | 10/2006 | Clarot et al. |
| 7,597,901 B2 | 10/2009 | Clarot et al. |
| 7,655,243 B2 | 2/2010 | Deem et al. |
| 7,674,904 B2 | 3/2010 | Doshan et al. |
| 8,105,817 B2 | 1/2012 | Deem et al. |
| 8,133,502 B2 | 3/2012 | Clarot et al. |
| 8,343,992 B2 | 1/2013 | Doshan et al. |
| 8,388,600 B1 | 3/2013 | Eldredge |
| 8,506,996 B2 | 8/2013 | Cronk et al. |
| 8,636,684 B2 | 1/2014 | Deem et al. |
| 8,852,224 B2 | 10/2014 | Cronk et al. |
| 9,211,253 B2 | 12/2015 | Crystal et al. |
| 9,468,747 B2 | 10/2016 | Crystal et al. |
| 9,480,644 B2 | 11/2016 | Crystal et al. |
| 9,511,210 B2 | 12/2016 | Deem et al. |
| 9,561,177 B2 | 2/2017 | Keegan et al. |
| 9,597,327 B2 | 3/2017 | Doshan et al. |
| 9,629,965 B2 | 4/2017 | Crystal et al. |
| 9,642,848 B2 | 5/2017 | Amancha et al. |
| 9,642,868 B2 | 5/2017 | Wei |
| 9,700,707 B2 | 7/2017 | Deem et al. |
| 9,707,226 B2 | 7/2017 | Keegan et al. |
| 9,775,838 B2 | 10/2017 | Keegan et al. |
| 9,956,232 B2 | 5/2018 | Wei |
| 10,052,465 B2 | 8/2018 | Deem et al. |
| 10,085,937 B2 | 10/2018 | Keegan et al. |
| 10,238,648 B2 | 3/2019 | Stinchcomb et al. |
| 10,441,538 B2 | 10/2019 | Amancha et al. |
| 10,653,690 B1 | 5/2020 | Savmarker et al. |
| 10,874,358 B2 | 12/2020 | Insler et al. |
| 11,020,343 B2 | 6/2021 | Strang et al. |
| 11,027,072 B2 | 6/2021 | Flather et al. |
| 11,191,934 B2 | 12/2021 | Mathai et al. |
| 11,202,757 B2 | 12/2021 | Temtsin-Krayz et al. |
| 11,202,894 B1 | 12/2021 | Thau et al. |
| 11,278,709 B1 | 3/2022 | Mathai et al. |
| 11,426,513 B2 | 8/2022 | Tyson |
| 11,628,139 B2 | 4/2023 | Amancha |
| 12,017,026 B2 * | 6/2024 | Mathai ............... A61K 31/485 |
| 2001/0004644 A1 | 6/2001 | Levin |
| 2004/0219107 A1 | 11/2004 | Clarot et al. |
| 2006/0275343 A1 | 12/2006 | Clarot et al. |
| 2007/0267011 A1 | 11/2007 | Deem et al. |
| 2008/0021369 A1 | 1/2008 | Deem et al. |
| 2008/0107475 A1 | 5/2008 | Wojcik et al. |
| 2010/0004628 A1 | 1/2010 | Clarot et al. |
| 2011/0027353 A1 | 2/2011 | Cronk et al. |
| 2011/0195455 A1 | 8/2011 | Benson et al. |
| 2011/0256070 A1 | 10/2011 | Martin et al. |
| 2012/0089078 A1 | 4/2012 | Deem et al. |
| 2013/0085472 A1 | 4/2013 | Shaari |
| 2013/0184684 A1 | 7/2013 | Yardley |
| 2013/0337031 A1 | 12/2013 | Kisak et al. |
| 2014/0114233 A1 | 4/2014 | Deem et al. |
| 2014/0155843 A1 | 10/2014 | Cronk et al. |
| 2015/0174061 A1 | 6/2015 | Wyse et al. |
| 2015/0265752 A1 | 9/2015 | Wei |
| 2015/0283091 A1 | 10/2015 | Vargas Rincon |
| 2015/0297617 A1 | 10/2015 | Given et al. |
| 2015/0297846 A1 | 10/2015 | Given et al. |
| 2015/0367115 A1 | 12/2015 | Deem et al. |
| 2016/0038406 A1 | 2/2016 | Hariharan |
| 2016/0058156 A1 | 3/2016 | Chiasson |
| 2016/0151257 A1 | 6/2016 | Klingman et al. |
| 2016/0158464 A1 | 6/2016 | Hijlkema et al. |
| 2016/0184564 A1 | 6/2016 | Spearman |
| 2016/0243188 A1 | 8/2016 | Shailubhai et al. |
| 2016/0339198 A1 | 11/2016 | Fraser et al. |
| 2016/0354363 A1 | 12/2016 | Amancha et al. |
| 2017/0020863 A1 | 1/2017 | Wright et al. |
| 2017/0042884 A1 | 2/2017 | Amancha et al. |
| 2017/0143096 A1 | 5/2017 | Zembrod |
| 2017/0165255 A1 | 6/2017 | Yum et al. |
| 2017/0189428 A1 | 7/2017 | Wei |
| 2017/0252337 A1 | 9/2017 | Amancha et al. |
| 2017/0266422 A1 | 9/2017 | Deem et al. |
| 2017/0296489 A1 | 10/2017 | Wei |
| 2017/0304192 A1 | 10/2017 | Strang et al. |
| 2017/0333688 A1 | 11/2017 | Parikh et al. |
| 2017/0348224 A1 | 12/2017 | Hariharan |
| 2018/0021771 A1 | 1/2018 | Tamir |
| 2018/0030405 A1 | 2/2018 | Subhadra |
| 2018/0133731 A1 | 5/2018 | Ritsche |
| 2018/0193332 A1 | 7/2018 | Loughlin et al. |
| 2019/0015323 A1 | 1/2019 | Keegan et al. |
| 2019/0038549 A1 | 2/2019 | Brecht |
| 2019/0070105 A1 | 3/2019 | Amancha et al. |
| 2019/0070396 A1 | 3/2019 | Johnson et al. |
| 2020/0306514 A1 | 10/2020 | Mathai et al. |
| 2020/0352934 A1 | 11/2020 | Loughlin et al. |
| 2021/0077382 A1 | 3/2021 | Crystal et al. |
| 2021/0128462 A1 | 5/2021 | Temtsin-Krayz et al. |
| 2021/0161835 A1 | 6/2021 | Presti |
| 2021/0186954 A1 | 6/2021 | Plucinski et al. |
| 2021/0228570 A1 | 7/2021 | Renger |
| 2021/0315552 A1 | 10/2021 | Kabaria et al. |
| 2021/0330903 A1 | 10/2021 | Patel |
| 2021/0338574 A1 | 11/2021 | Strang et al. |
| 2021/0401827 A1 | 12/2021 | Crystal et al. |
| 2022/0016026 A1 | 1/2022 | McCarty |
| 2022/0160618 A1 | 5/2022 | Boyer et al. |
| 2022/0241268 A1 | 8/2022 | Pergolizzi |
| 2022/0313686 A1 | 10/2022 | Barenholz et al. |
| 2022/0313687 A1 | 10/2022 | Li et al. |
| 2022/0387421 A1 | 12/2022 | Plucinski et al. |
| 2023/0001084 A1 | 1/2023 | Lee et al. |
| 2023/0095235 A1 | 3/2023 | Huang et al. |
| 2023/0149388 A1 | 5/2023 | Fukhari et al. |

FOREIGN PATENT DOCUMENTS

| | | |
|---|---|---|
| EP | 3 082 816 B1 | 3/2019 |
| WO | 1996/09047 A1 | 3/1996 |
| WO | 1999/53841 A1 | 10/1999 |
| WO | 2000/62757 A1 | 10/2000 |
| WO | 2004/024225 A1 | 3/2004 |
| WO | 2004/024226 A1 | 3/2004 |
| WO | 2006/098650 A1 | 9/2006 |
| WO | 2007/126851 A2 | 11/2007 |
| WO | 2007/137235 A2 | 11/2007 |
| WO | 2009/040595 A1 | 4/2009 |
| WO | 2009/067536 A2 | 5/2009 |
| WO | 2012/156317 A2 | 11/2012 |
| WO | 2014/076569 A2 | 5/2014 |

(56) References Cited

FOREIGN PATENT DOCUMENTS

| WO | 2014/121342 | A1 | 8/2014 |
|---|---|---|---|
| WO | 2016/007729 | A1 | 1/2016 |
| WO | 2016/132223 | A1 | 8/2016 |
| WO | 2017/218854 | A1 | 12/2017 |
| WO | 2017/223566 | A1 | 12/2017 |
| WO | 2018/064672 | A1 | 4/2018 |
| WO | 2018/089709 | A1 | 5/2018 |
| WO | 2018/093666 | A1 | 5/2018 |
| WO | 2019/005759 | A1 | 1/2019 |
| WO | 2019/048527 | A1 | 3/2019 |
| WO | 2019/074701 | A1 | 4/2019 |
| WO | 2020/198327 | A1 | 10/2020 |
| WO | 2021/225973 | A1 | 11/2021 |

OTHER PUBLICATIONS

Esposito et al., "Collection by trained pediatricians or parents of mid-turbinate nasal flocked swabs for the detection of influenza viruses in childhood", Virology Journal, Jan. 1, 2010, vol. 7, No. 85, 4 pages.

Djupesland, "Nasal drug delivery devices: characteristics and performance in a clinical perspective—a review", Drug Delivery and Translational Research, Oct. 18, 2012, vol. 3, No. 1, pp. 42-62.

Jeong et al., Biodegradable block copolymers as injectable drug-delivery systems, Nature 388:860-862 (1997).

Jeong et al., Drug release from biodegradable injectable thermosensitive hydrogel of PEGPLGA-PEG triblock copolymers, Journal of Controlled Release, 63:155-163 (2000).

Jeong et al., Thermosensitive sol-gel reversible hydrogels, Advanced Drug Delivery Reviews, 54:37-51 (2002).

International Search Report and Written Opinion for PCT Application No. PCT/US2020/024661 dated Jun. 16, 2020, 35 pages.

International Preliminary Report on Patentability for PCT Application No. PCT/US2020/024661 dated Sep. 28, 2021, 31 pages.

International Search Report and Written Opinion for PCT/US2022/019918 dated Jun. 14, 2022, 17 pages.

International Preliminary Report on Patentability for PCT Application No. PCT/US2022/019918 dated Sep. 12, 2023, 8 pages.

Non-Final Office Action mailed on Jul. 21, 2020, in U.S. Appl. No. 16/831,555, 11 pages.

Final Office Action mailed on Nov. 20, 2020, in U.S. Appl. No. 16/831,555, 15 pages.

Non-Final Office Action mailed on Mar. 8, 2021, in U.S. Appl. No. 16/831,555, 9 pages.

Final Office Action mailed on Jun. 7, 2021, in U.S. Appl. No. 16/831,555, 9 pages.

Notice of Allowance mailed on Oct. 27, 2021, in U.S. Appl. No. 16/831,555, 11 pages.

Non-Final Office Action mailed on Jan. 26, 2022, in U.S. Appl. No. 17/523,321, 10 pages.

Final Office Action mailed on Apr. 4, 2022, in U.S. Appl. No. 17/523,321, 9 pages.

Non-Final Office Action mailed on Sep. 15, 2022, in U.S. Appl. No. 17/523,321, 11 pages.

Final Office Action mailed on Apr. 10, 2023, in U.S. Appl. No. 17/523,321, 12 pages.

Notice of Allowance mailed on Dec. 1, 2021, in U.S. Application No. 17/463,0795, 9 pages.

Non-Final Office Action mailed on May 12, 2022, in U.S. Appl. No. 17/682,261, 23 pages.

Final Office Action mailed on Sep. 14, 2022, in U.S. Appl. No. 17/682,261, 25 pages.

Non-Final Office Action mailed on Apr. 7, 2023, in U.S. Appl. No. 17/682,261, 23 pages.

Notice of Allowance mailed on Feb. 12, 2024, in U.S. Appl. No. 17/682,261, 9 pages.

\* cited by examiner

PK Data

| Dose Route | Dosage | Partial AUC (pgxhr/mL) | | | AUC | Cmax | T-1/2 | Tmax | |
|---|---|---|---|---|---|---|---|---|---|
| | | AUC0.04 2.4 mins | AUC0.08 4.8 mins | AUC0.17 10 mins | AUClast pg x hr/mL | pg/mL | Hours | Hours | Mins |
| Treatment 1 | 0.4mg | 4.19 | 20.7 | 98.28 | 1410.71 | 1279.75 | 1.26 | 0.25 | 15 |
| Treatment 2 | 4mg | 11.81 | 67.56 | 355.66 | 8589.48 | 5551.21 | 1.51 | 0.45 | 27 |
| Treatment 3 | ~20% released | 29.16 | 83.77 | 174.47 | 816.45 | 1575.45 | 1.38 | 0.07 | 4.2 |
| Treatment 4 | ~20% released | 14.61 | 46.44 | 106.78 | 521.15 | 932.09 | 1.63 | 0.09 | 5.4 |
| Treatment 5 | ~20% released | 15.62 | 56.76 | 155.36 | 1120.82 | 1319.53 | 1.85 | 0.14 | 8.4 |

FIG. 7

| | ADMINISTRATION TECHNIQUES | # NOSTRILS |
|---|---|---|
| 1 | INSERT APPLICATOR, PINCH NOSE WITH THUMB AND FOREFINGER FOR 5 SECONDS, REMOVE APPLICATOR | ONE |
| | | TWO |
| 2 | INSERT APPLICATOR, PINCH NOSE WITH THUMB AND FOREFINGER FOR 20 SECONDS, REMOVE APPLICATOR | ONE |
| | | TWO |
| 3 | INSERT APPLICATOR, PINCH NOSE WITH THUMB AND FOREFINGER FOR 5 SECONDS, STOP PINCHING BUT KEEP APPLICATOR IN NOSE FOR ADDITIONAL 15 SECONDS | ONE |
| | | TWO |
| 4 | INSERT APPLICATOR, PINCH NOSE WITH THUMB AND FOREFINGER FOR 20 SECONDS, STOP PINCHING BUT KEEP APPLICATOR IN NOSE FOR ADDITIONAL 15 SECONDS | ONE |
| | | TWO |
| 5 | INSERT APPLICATOR INTO NOSTRIL AND PRESS AGAINST SIDE FOR 20 SECONDS | ONE |
| | | TWO |
| 6 | SWIRL APPLICATOR 12 TIMES IN ONE NOSE | ONE |
| | | |
| 7 | SWIRL APPLICATOR 3 OR MORE TIMES IN EACH NOSE | |
| | | TWO |
| 8 | SWIRL APPLICATOR 3 TIMES WHILE PINCHING NOSE | ONE |
| | | TWO |

FIG. 8

DRUG DELIVERY DEVICE AND METHODS FOR USING SAME

This application is a continuation of U.S. application Ser. No. 17/682,261, filed on Feb. 28, 2022, now allowed, which is a continuation of U.S. application Ser. No. 17/463,079, filed on Aug. 31, 2021, which issued as U.S. Pat. No. 11,278,709, which claims the benefit under 35 U.S.C. § 119(c) of U.S. Provisional Application No. 63/177,772, filed on Apr. 21, 2021 and U.S. Provisional Application No. 63/160,563, filed on Mar. 12, 2021, each of which is incorporated by reference in its entirety.

FIELD

The invention relates to devices for intranasal administration of naloxone and methods of using the devices for treating an opioid overdose. The devices comprise a foam applicator and are configured to locate an applicator comprising a naloxone composition in proximity to the middle turbinate and/or inferior turbinate. Naloxone can be delivered to the nasal mucosa by squeezing the nostril against the applicator. The device and methods of using the devices can be used to treat an opioid overdose.

BACKGROUND

Naloxone antagonizes opioid effects by competing for opioid receptor sites. Naloxone reverses the effects of opioids, including respiratory depression, sedation, and hypotension. Naloxone can also reverse the psychotomimetic and dysphoric effects of agonist-antagonists such as pentazocine.

Naloxone, first approved by the Food and Drug Administration (FDA) in 1971, is a safe and effective opioid antagonist used to treat and reverse opioid overdoses. Currently, there are two prescription naloxone products, an intranasal spray and an intramuscular (IM) autoinjector, available for non-medically trained individuals such as families, caregivers, and friends of those at risk of an opioid overdose.

Naloxone hydrochloride nasal spray is indicated for the emergency treatment of a known or suspected opioid overdose, as manifested by respiratory and/or central nervous system depression. Naloxone hydrochloride nasal spray is intended for immediate administration as emergency therapy in settings where opioids may be present. The recommended initial dose of naloxone hydrochloride nasal spray in adults is a single spray delivered by intranasal administration into one nostril.

Following a single intranasal administration of naloxone hydrochloride nasal spray at a dose of 2 or 4 mg, the mean plasma half-life of naloxone in healthy adults is about 1.85 hours (33% coefficient of variation (CV)) and 2.08 hours (30% CV); respectively, which is longer than that observed after administration of a 0.4 mg naloxone hydrochloride by IM injection, where the half-life is 1.24 hours (26% CV).

Intranasal administration of naloxone hydrochloride is a clinically effective method for treating an opioid overdose. Intranasal administration can provide for rapid absorption and onset of action; high plasma bioavailability; direct transport to central nervous system from the highly vascularized venous regions of the nasal mucosa to the cardiopulmonary system then quickly to the brain; limited need for intravenous access; and ease of use and familiarity for consumers, as well as health care professionals.

The recent increase in opioid overdose deaths has been attributed to the emergence of highly potent synthetic opioids, such as fentanyl. Improved devices and methods for internally administering naloxone hydrochloride to treat an opioid overdose is desired.

SUMMARY

According to the present invention, devices for administering naloxone to a patient comprise: a handle comprising a proximate end and a distal end; a nasal stop attached to the handle toward the distal end; and an applicator coupled to the distal end, wherein the applicator comprises a foam, wherein the distance between the nasal stop and the distal end of the applicator is from 15 mm to 31 mm.

According to the present invention, methods for treating an opioid overdose in a patient comprise: (a) inserting the applicator of the device according to the present invention into the nasal cavity of a nostril of a patient having an opioid overdose; (b) bringing the stop into contact with the anterior naris to situate the applicator in proximity to the middle turbinate and the inferior turbinate; and (c) squeezing the nostril against the applicator for from 1 seconds to 5 seconds to release the naloxone hydrochloride composition from the applicator and to administer the naloxone hydrochloride composition to the nasal mucosa, to thereby treat the opioid overdose.

BRIEF DESCRIPTION OF THE DRAWINGS

Those skilled in the art will understand that the drawings described herein are for illustration purposes only. The drawings are not intended to limit the scope of the present disclosure.

FIG. 2A shows a device enclosed within a foil envelope. FIG. 2B shows a device partially exposed with a foil envelope partially pulled back.

FIG. 7 shows a table summarizing the PK parameters for the PK profiles shown in FIGS. 5 and 6.

FIG. 8 shows a table with examples of administration methods intended to reduce the amount of residual naloxone composition remaining on the applicator after administration.

DETAILED DESCRIPTION

Figure 1A:
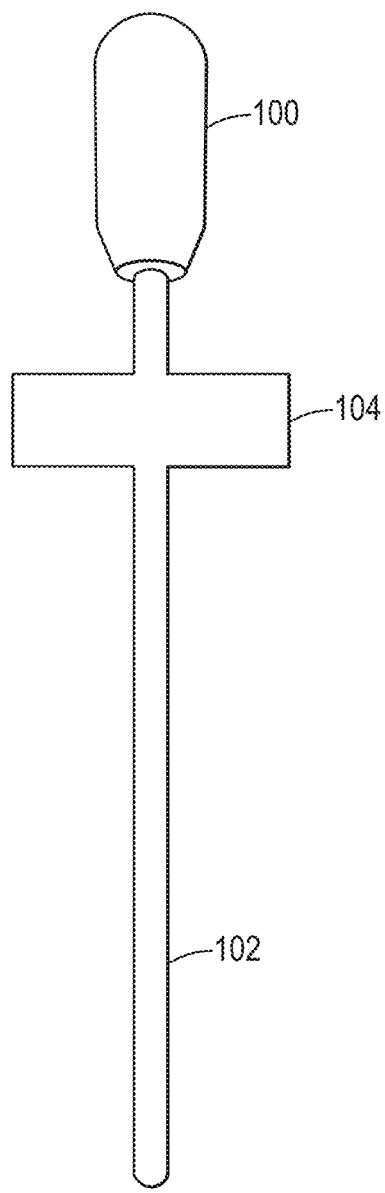
FIG. 1A shows an example of a device provided by the present disclosure.

Described herein are devices and methods for delivering naloxone hydrochloride to a patient having an opioid overdose.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Dose of naloxone hydrochloride refers to the amount of naloxone delivered to the nasal mucosa using the devices and methods provided by the present disclosure. The dose of naloxone hydrochloride delivered can be determined by comparing the amount of naloxone hydrochloride initially retained by an applicator with the amount of naloxone hydrochloride remaining on the applicator after administration of the naloxone hydrochloride composition to the nasal mucosa. The dose of naloxone hydrochloride delivered by an applicator dose not necessarily correspond to the amount of naloxone absorbed by the nasal mucosa and entering the systemic circulation of a patient.

"$C_{max}$" refers to the maximum observed concentration occurring at time $T_{max}$.

"$T_{max}$" refers to the time to reach the maximum plasma concentration $C_{max}$.

"$AUC_{0-tlast}$" refers to the area under the plasma concentration-time curve from time 0 to the time of the last quantifiable concentration.

"$AUC_{0-inf}$" refers to the area under the plasma concentration-time curve from time 0 to infinite time, calculated as the sum of $AUC_{0-tlast}$ and $C_{last}/\lambda z$.

"$AUC_{0-\tau}$" refers to the area under the plasma concentration-time curve during a dosing interval $\tau$. For example, the interval can be 6 hours or 8 hours after dosing.

$pAUC_t$ refers to the partial area under the curve from time 0 to time t minutes following administration.

"$\lambda z$" refers to the apparent terminal elimination rate constant.

"$T_{1/2}$" refers to the elimination half-life associated with the terminal slope ($\lambda z$) of the semilogarithmic drug concentration-time curve, calculated as $0.693/\lambda z$.

"Naloxone composition" refers to a pharmaceutical composition comprising naloxone hydrochloride.

"Bioequivalent" refers to a formulation and/or pharmaceutical composition that is therapeutically equivalent to a reference product when administered under the same conditions in a pharmacokinetic evaluation conforming to FDA Guidance on Bioequivalence Testing; regardless of biopharmaceutical class.

A value that is "bioequivalent" refers to a pharmacokinetic value such as the $C_{max}$ or AUC that exhibits substantially similar pharmacokinetic profiles and/or therapeutic effects. Bioequivalence may be demonstrated by several in vivo and in vitro methods. These methods may include, for example, pharmacokinetic, pharmacodynamic, clinical and in vitro studies. Bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. In some embodiments, a value is bioequivalent to a reference pharmacokinetic value when the geometric mean of the AUC and/or the $C_{max}$ is between 80% and 125% (e.g., at 90% confidence interval) of the reference pharmacokinetic value.

A similar or bioequivalent pharmacokinetic profile refers to a pharmacokinetic profile for which the mean $AUC_{0-inf}$ of a pharmaceutical composition is from 80% to 125% of the mean $AUC_{0-Inf}$ a reference composition in a suitably designed cross-over trial, the mean plasma concentration at 8 hours $C_{8h}$ of the pharmaceutical composition is from 40% to 130% of the mean plasma concentration at 8 hours $C_{8h}$ of the reference composition, and/or that the maximum plasma concentration ($C_{max}$) of the pharmaceutical composition is from 50% to 140% of the $C_{max}$ of the reference composition.

"Treating" an opioid overdose refers to reversing the cause of an opioid overdose. For example, naloxone acts as an opioid antagonist and reverses the cause of an opioid overdose by binding to opioid receptors and blocks the effects of other opioids. For example, an opioid antagonist such as naloxone can restore normal breathing in a person having an opioid overdose.

"Therapeutically effective amount" refers to the amount of a pharmaceutically active ingredient such as naloxone for treating an opioid overdose.

"Therapeutically effective dose" refers to a dose of naloxone hydrochloride that is effective in reversing the effects of an opioid overdose. A therapeutically effective dose may be determined in accordance with routine pharmacological procedures known to those skilled in the art.

Reference is now made to certain devices and methods. The disclosed embodiments are not intended to be limiting of the claims. To the contrary, the claims are intended to cover all alternatives, modifications, and equivalents.

Described herein is a device and a method for intranasal administration of naloxone hydrochloride. Embodiments of a device provided by the present disclosure include an applicator that is configured to hold a naloxone composition in a manner so that when the device is placed within proximity to or within direct contact with the nasal mucosal, the naloxone composition is released from the applicator onto the nasal mucosa accurately and reproducibly. As such, embodiments, of a device provided by the present disclosure are configured to both hold a naloxone composition and release the naloxone composition onto the nasal mucosa when used with a pre-determined accuracy and precision. A device provided by the present disclosure is configured to hold a naloxone composition on a surface of the device and release the naloxone composition onto a nasal mucosa located within a nasal passage with a pre-determined accuracy and precision. Release of the naloxone composition may be a total release, such as release the total amount of the naloxone composition initially held by the device or a partial release of the naloxone composition, such as release of less than the total amount of the naloxone composition that is held by the device to meet a pre-determined accuracy and precision.

Both a device and method provided by the present disclosure are suitable for intranasally administering a naloxone composition to a patient in need thereof, such as a patient having an opioid overdose. A device and method provided by the present disclosure can be used for the administration of a naloxone composition to an individual in an emergency situation. For example, a device and method provided by the present disclosure can be used for delivering naloxone hydrochloride to an individual experiencing an opioid overdose.

A device provided by the present disclosure comprises an applicator configured to hold a naloxone composition and release the naloxone composition onto the nasal mucosa. Release of the naloxone composition onto the nasal mucosa can occur when the applicator holding the naloxone composition contacts the nasal mucosa. Pressure can be applied to the applicator during contact with the nasal mucosa to cause release of the naloxone composition onto the nasal mucosa. Contact such as a very light force applied to the applicator can result in the release of the naloxone composition onto the nasal mucosa.

The material properties of the applicator facilitate achieving the desired accuracy and precision in dosing. A material can hold or retain a naloxone composition in a way that when released, a pre-determined accuracy and precision is consistently achieved.

A device for delivering naloxone hydrochloride to the nasal mucosa of an individual can comprise: (a) an applicator comprising a polyurethane foam; (b) 70 μL to 350 μL of a naloxone composition that is held by the applicator, (c) a handle attached to the applicator; and wherein the polyurethane applicator has a pore count from 60 pores/in to 100 pores/in, a pore size of 0.01 in to 0.0167 in (0.25 mm to 0.42 mm) and a density of from 1.7 lb/ft$^3$ to 2.5 lb/ft$^3$ (27 kg/m3 to 40.0 kg/m$^3$). In some embodiments, the polyurethane is reticulated foam. In some embodiments, the naloxone composition comprises 60 mg/mL of naloxone hydrochloride. A device can comprise an applicator configured to release, for example, from 1 mg to 20 mg of naloxone hydrochloride such as from 4 mg to 20 mg of naloxone hydrochloride with a RSD (relative standard deviation) less than 6% for a single use of the device. A device can include a stop that is attached to the handle and is configured such that during use the applicator is situated in proximity to the middle turbinate and/or the inferior turbinate. A device can be at least partially enclosed in a secondary container closure system such as a foil envelope.

Described herein is a method for delivering naloxone hydrochloride to the nasal mucosa of an individual in need of treatment with naloxone hydrochloride, comprising: (a) receiving a device having an applicator and a handle. wherein the applicator comprises a polyurethane foam that holds from 70 μL to 350 μL of a liquid composition containing the naloxone; (b) inserting the device into a nasal passage of the individual; and (c) releasing the naloxone composition containing onto the nasal mucosa of the individual by contacting the nasal mucosa of the individual with the applicator. In some embodiments. the applicator comprises a polyurethane foam having a pore count from 60 pores/in to 100 pores/in, pore size of 0.01 in to 0.0167 in, and a density of from 1.7 lb/ft$^3$ to 2.5 lb/ft$^3$ (27 kg/m$^3$ to 40.0 kg/m$^3$). In some embodiments, the polyurethane foam is a reticulated polyurethane foam. In some embodiments, the naloxone composition comprises a naloxone hydrochloride concentration from 40 mg/mL to 80 mg/mL, such as from 50 mg/mL to 80 mg/mL or from 50 mg/mL to 70 mg/mL such as 60 mg/mL. In some embodiments, releasing the naloxone composition onto the nasal mucosa of the individual results in release of from 4 mg to 20 mg of naloxone hydrochloride with a (RSD) relative standard deviation less than 6% in a single use of the applicator. In some embodiments, the device includes a stop that is attached to the handle and positions the applicator in proximity to the middle turbinate and/or the inferior turbinate and prevents the applicator from advancing deep into the nasal passage when the stop contacts a nostril of the individual. In some embodiments, the method comprises the step of removing the device from a secondary container closure system such as a foil envelope, wherein the step is carried out after step (a). In some embodiments, an individual who carries out step (b) is a different individual than the individual in need of treatment with naloxone hydrochloride. In some embodiments, step (c) is carried out a single time, and wherein carrying out step (c) the single time results in release of from 4 mg to 20 mg of naloxone hydrochloride with a relative standard deviation (RSD) less than 6% onto the nasal mucosa of the individual. In some embodiments, step (c) results in release of at least 80% of the volume of the naloxone composition initially retained by the application from the applicator during administration. In some embodiments, an amount of naloxone hydrochloride released onto the nasal mucosa in step (c) increases linearly as the amount of the naloxone composition held by the applicator increases.

Direct application using a device having a nasal applicator was developed to target the highly vascularized anterior region of the nasal mucosa proximate the middle turbinate and/or inferior turbinate (respiratory epithelium), which has a large surface area of from 120 cm$^2$ to 150 cm$^2$ and is believed to be the main site of naloxone hydrochloride absorption.

A device provided by the present disclosure includes an applicator and a handle. In some embodiments, the device further includes a nasal stop configured to prevent the applicator from traveling past a certain point within the nasal cavity. A device can include a cap configured to at least partially cover the applicator prior to use. A device can include a secondary container closure system such as a wrapper or pouch that seals the device within it or at least partially seals the device within it.

A device provided by the present disclosure can be configured to hold and release a naloxone composition and in some embodiments the device is configured to one or more active pharmaceutical ingredients in addition to naloxone hydrochloride.

A device provided by the present disclosure dose not penetrate or abrade a nasal mucosa upon which the applicator delivers a naloxone composition. That is, in these embodiments, a device provided by the present disclosure does not inject a naloxone composition into the nasal mucosa. For example, embodiments of a device provided by the present disclosure do not include penetrating components such as microneedles but rather release a naloxone composition onto the surface of the nasal mucosa without penetrating that tissue.

FIG. 1A shows an example of a device provided by the present disclosure. In this example the device comprises an applicator 100, a handle 102, and a stop 104. As described below in greater detail, an applicator 100 is configured to both hold and release a naloxone composition. The applicator 100 shown in FIG. 1A has the shape of a swab, the swab having an oblong bulbous shape. An applicator 100 can hold a naloxone composition and can release a naloxone composition. An applicator 100 can be configured to release a naloxone composition in a way that is reproducible and reliable such that each device that includes the same applicator 100 will have a similar release profile. A handle 102 is described in greater below and is in general configured to provide a handhold for an individual to use to direct the applicator toward a target site such as, for example, the nasal mucosa at the tip of the middle turbinate and/or inferior turbinate. A stop 104 can be sized and positioned at a location along the handle so that the applicator is directed proximate to the intranasal target site and is prevented from being advanced too far into the nasal passage by physically blocking further advance. In the example shown in FIG. 1A is configured for insertion into a nasal passage, and as such the stop 104 has a diameter that is wider than a nostril diameter so that the stop contacts the exterior of the nostril when the applicator is inserted into the nasal cavity and blocks advance of the device into the nasal cavity past the location of the stop 104. A stop can be configured to protect an individual receiving the naloxone therapy by the applicator 102 from an injury caused by the applicator being inserted too far into the nasal passage. A device provided by the present disclosure can include an applicator 100 and a handle 102, and in certain embodiments a device can further include a stop 104.

A handle and stop can be made of any suitable material such as a thermoplastic or thermoset.

A suitable thermoplastic or thermoset can be sterilizable and can be selected from a sterilizable grade of a thermoplastic or thermoset.

Examples of suitable thermoplastics include polypropylene, polyethylene, polyurethane, and combinations of any of the foregoing.

A device provided by the present disclosure can have dimensions configured to deliver a naloxone composition to the nasal mucosa in the region of the nasal cavity proximate to the middle turbinate and/or the inferior turbinate. This region of the nasal cavity is highly vascularized and thereby can facilitate absorption of an applied pharmaceutical composition into the systemic circulation.

Figure 11A:
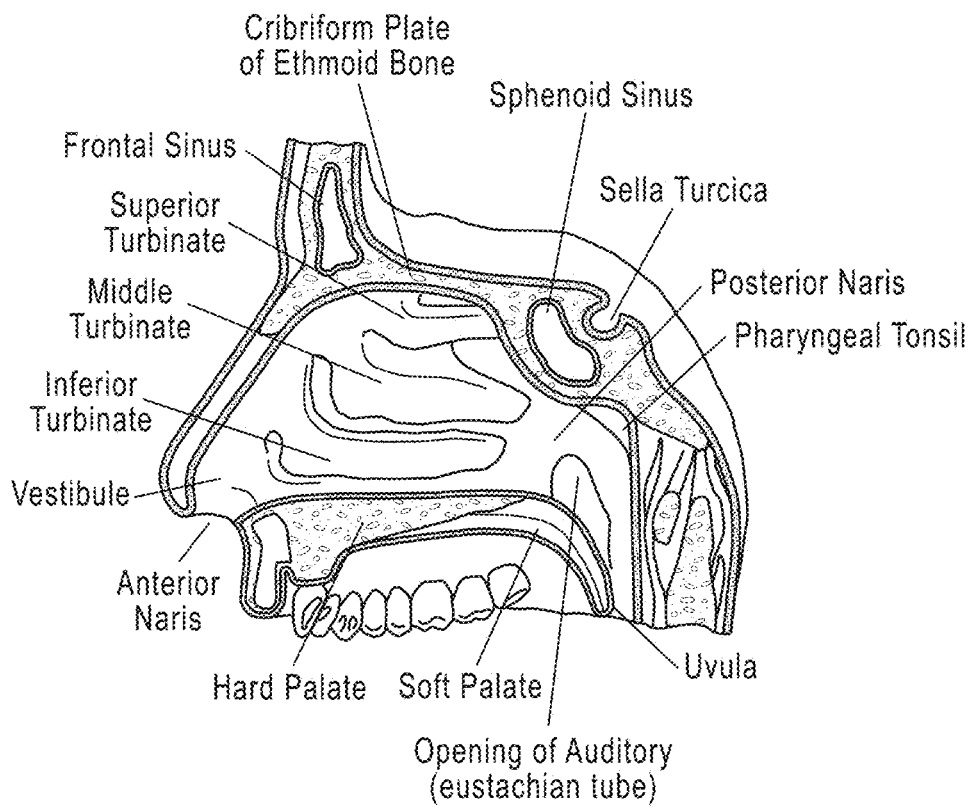
FIG. 11A is an illustration showing the anatomy of the nose.

A cross-sectional profile of the human nasal cavity is provided in FIG. 11A. The tip of the middle turbinate and the tip of the inferior turbinate are located about 15 mm and about 25 mm, respectively, from the anterior naris (nasal opening). The tip of the anterior turbinate is located about 35 mm from the nasal opening. The nasal opening of an adult human has a diameter from about 10 mm to about 12 mm.

Figure 11B:
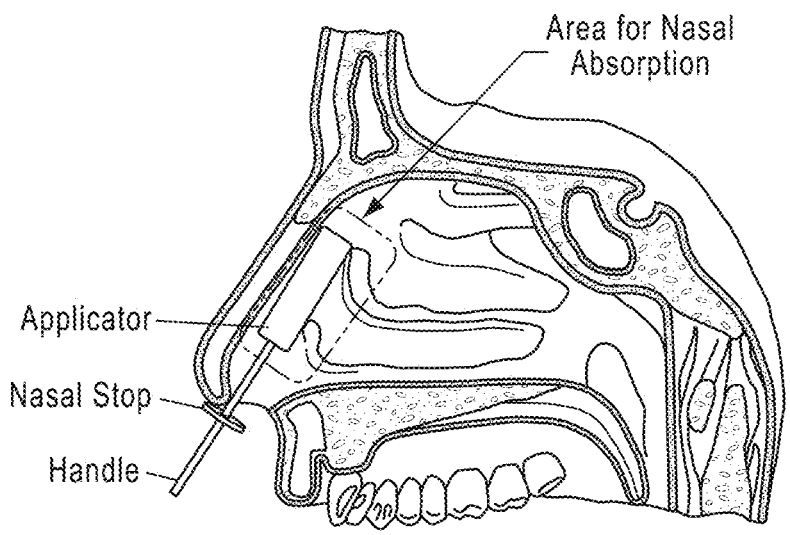
FIG. 11B is an illustration showing a cross-section of the nose with a device provided by the present disclosure having an applicator situated within the nasal cavity and proximate the middle turbinate and the inferior turbinate.

As shown in FIG. 11B, an applicator provided by the present disclosure can be inserted into the nasal vestibule through the nasal opening such that the applicator is adjacent the middle turbinate and/or the inferior turbinate. The stop of the device sets the position of the applicator within the nasal cavity during use.

Figure 12A:
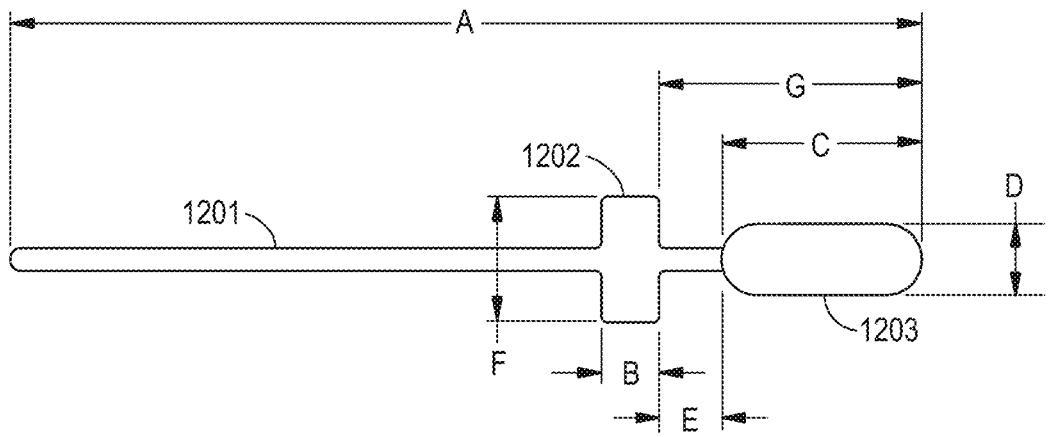
FIGS. 12A-12C show views of an example of a device provided present disclosure.
Figure 12B:
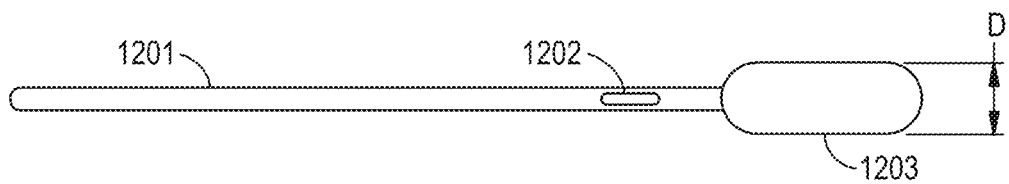

FIGS. 12A and 12B show dimensions for an example of a device provided by the present disclosure.

A handle can be of any suitable dimension to facilitate insertion of the applicator into the nasal cavity. Referring to FIG. 12A, in a device provided by the present disclosure the handle 1201 can have a total length A, for example, from 3 in to 5 in (76 mm to 127 mm), such as from 3.25 in to 4.75 in (82 mm to 121 mm), from 3.5 in to 4.5 in 89 mm to 114 mm), or from 3.75 in to 4.25 in (95 m to 108 mm).

A stop 1202 can be situated to facilitate the ability of the applicator to contact the nasal mucosa in the region of the middle turbinate and inferior turbinate. A stop 1202 can have any suitable width B such as to cause the stop to rest against the anterior naris during use and resist further penetration of the applicator into the nasal cavity. A stop has a width that is wider than the nostril opening of a patient. The stop can be in the shape, for example, of a substantially flat tab or can be in the shape of a disc surrounding the handle. Referring to FIG. 12A, in a device provided by the present disclosure a stop can have a width F, for example, from 0.3 in to 0.7 in (7 mm to 18 mm), such as from 0.35 in to 0.65 in (9 mm to 16 mm), from 0.4 in to 0.6 in (10 mm to 15 mm), or from 0.45 in to 0.55 in (11 mm to 14 mm). A stop can have a width F, for example, greater than 9 mm, greater than 10 mm, greater than 12 mm, greater than 14 mm, or greater than 16 mm. A stop can have a length B, for example, from about 0.2 in to 0.4 in (5 mm to 10 mm).

Referring to FIG. 12A, in a device provided by the present disclosure an applicator 1203 can have a length C, for example, from 0.7 in to 1.1 in (18 mm to 28 mm), such as from 0.75 in to 1.05 in (19 mm to 27 mm), from 0.8 in to 1.0 in (20 mm to 25 mm), or from 0.85 in to 0.95 in (21 mm to 24 mm).

Referring to FIG. 12A, in a device provided by the present disclosure an applicator 1203 can have a width (diameter) D, for example, from 0.15 in to 0.45 in (3.8 mm to 11.4 mm), such as from 0.2 in to 0.4 in (5.1 mm to 10.2 mm), or from 0.25 in to 0.35 in (6.35 mm to 8.9 mm).

Referring to FIG. 12A, in a device provided by the present disclosure the distance E between the stop 1202 and the proximate edge of the applicator 1203 can be, for example, from 0.15 in to 0.45 in (3.8 mm to 11.4 mm), such as from 0.2 in to 0.4 in (5.1 mm to 10.2 mm), or from 0.25 in to 0.35 in (6.35 mm to 8.9 mm).

Referring to FIG. 12A, in a device provided by the present disclosure the distance G between the stop 1202 and the distal edge of the applicator 1203 can be, for example, from 0.9 in to 1.5 in (23 mm to 38 mm), such as from 1.0 in to 1.4 in (25.4 mm to 35.6 mm), or from 1.1 in to 1.3 in (27.9 mm to 33 mm).

Referring to FIG. 12A, in a device provided by the present disclosure, for example, the handle 1201 can have a length A from 3 in to 5 in (76 mm to 127 mm), the stop 1202 can have a width F from 0.4 in to 0.6 in (10.2 mm to 15.2 mm), the applicator can have a length C from 0.7 in to 1.1 in (17.8 mm to 27.9 mm), the applicator 1203 can have a width D from 0.2 in to 0.4 in (5.1 mm to 10.2 mm), the distance between the stop and the proximate edge of the applicator can be from 0.2 in to 0.4 in (5.1 mm to 10.2 mm), and the distance between the stop and the distal end of the applicator can be from 1.0 in to 1.4 in (25.4 mm to 35.6 mm).

Referring to FIG. 12A, in a device provided by the present disclosure, for example, the handle can have a length A of 4 in (102 mm), the stop can have a width F of 0.5 in (12.7 mm), the applicator can have a length C of 0.9 in (22.9 mm), the applicator can have a width D of 0.3 in (7.6 mm), the distance E between the stop and the proximate edge of the applicator can be 0.3 in (7.6 mm), and the distance between the stop and the distal end of the applicator can be 1.2 in (30.5 mm).

Figure 12C:
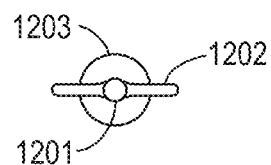

The device, and in particular the distance between the stop and the proximate edge of the applicator and between the stop and the distal edge of the applicator, can be configured to position the applicator in adjacent the respiratory mucosa in proximity to the tip of the middle turbinate and the inferior turbinate, which is 1.5 cm to 3 cm from the anterior naris and the nasal opening. FIGS. 12B and 12C show other views of the device shown in FIG. 12A.

Figure 1B:
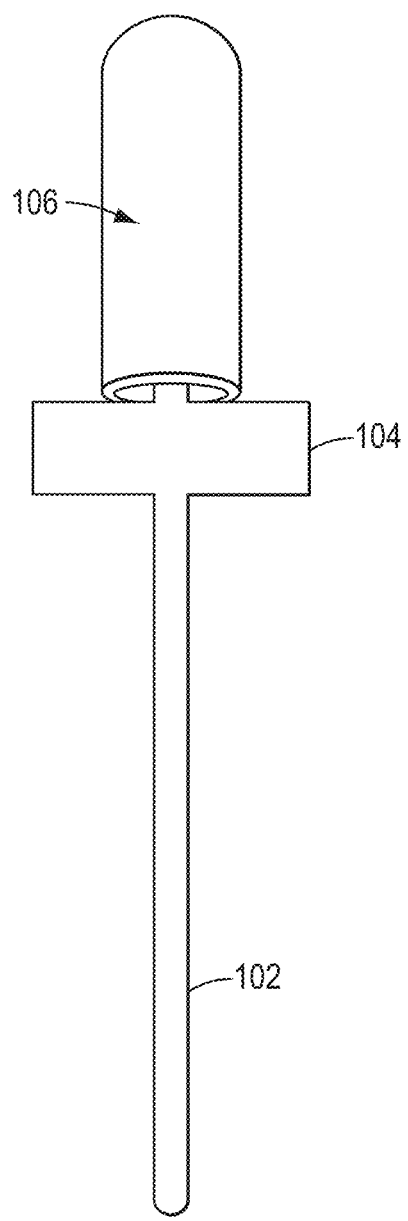
FIG. 1B shows an example of the device of FIG. 1A with a removable cap 106 on top of and covering the applicator of the device, which also includes a handle and a stop.

FIG. 1B shows an embodiment of the device shown in FIG. 1A with a removable cap 106 covering the applicator of the device, and also shows a handle 102 and a stop 104. The removable cap can protect the applicator before use and can be removed before use such as immediately before use.

A removable cap provided by the present disclosure can be made using any suitable material such as a thermoplastic or thermoset. A removable can be made from the same material used to fabricate the handle and stop. The removeable can be made from a sterilizable material such as a sterilizable grade of thermoplastic or sterilizable grade of thermoset. A removeable cap can be dimensioned to cover and protect the applicator during storage and removed without damaging the applicator. A removable cap can comprise, for example, polypropylene or polyethylene.

The applicator of a provided by the present disclosure can be configured to hold and release a naloxone composition. The mechanism of holding and/or releasing a naloxone composition may include any suitable mechanical and/or chemical mechanism including, for example, absorption, capillary action, adsorption, chemical binding such as covalent and ionic, electrostatic coupling, and/or magnetic coupling.

An applicator can hold or retain a naloxone composition on a surface of the applicator and/or interior surfaces and/or voids within the applicator in such a manner that the naloxone composition is retained in a stable form for a duration and is releasable from the applicator when the applicator is used. An applicator can be configured to hold a naloxone formulation for a duration until the naloxone formulation is caused to be released from the applicator. A duration over which a naloxone formulation can be held by an applicator provided by the present disclosure may be, for example, at least 15 minutes. A duration over which a naloxone composition can be held by an applicator may be at least 30 minutes. A duration over which a naloxone composition can be held by an applicator may be at least 1 hour. A duration over which a naloxone composition can be held by an applicator may be at least 2 hours. A duration over which a naloxone composition can be held by an applicator may be at least 5 hours. A duration over which a naloxone composition can be held by an applicator may be at least 10 hours. A duration over which a naloxone composition can be held by an applicator may be at least 1 day. A duration over which a naloxone composition can be held by an applicator may be at least one week. A duration over which a naloxone composition can be held by an applicator may be at least 1 month. A duration over which a naloxone composition can be held by an applicator may be at least 2 months. A duration over which a naloxone composition can be held by an applicator may be at least 3 months. A duration over which a naloxone composition can be held by an applicator may be at least 6 months. A duration over which a naloxone composition can be held by an applicator may be at least 9 months. A duration over which a naloxone composition can be held by an applicator may be at least 1 year. A duration over which a naloxone composition can be held by an applicator may be at least 2 years. A duration over which a naloxone composition can be held by an applicator may be at least 5 years.

An applicator suitable for use with devices provided by the present disclosure can have various geometric shapes, both regular shapes and irregular shapes. In some embodiments, an applicator is shaped as a swab having a bulbous tapering shape. Examples of applicator shapes suitable for use with embodiments of the device described herein include spheroid, ovoid, cuboid, cylindrical, pyramid, and diamond.

A material suitable for an applicator can be any material that has both an ability to hold a naloxone composition and an ability to release the naloxone composition. An applicator can comprise a material that holds 100% of a naloxone composition and releases 100% of a naloxone composition when contacted to a surface, where percent (%) is based on the total weight and/or the total volume of the naloxone composition and can be determined using gravimetric analysis. An applicator can comprise a material that holds 100% of a naloxone composition and releases from 95% to 100% of a naloxone composition when contacted to a surface. where percent (%) is based on the total weight and/or the total volume of the naloxone composition. An applicator can comprise a material that holds 100% of a naloxone composition and releases from 90% to -95% of a naloxone composition when contacted to a surface, where percent (%) is based on the total weight and/or the total volume of the naloxone composition. An applicator can comprise a material that holds 100% of a naloxone composition and releases from 85% to -90% of the naloxone composition when contacted to a surface, where percent (%) is based on the total weight and/or the total volume of the naloxone composition. It should be understood that the performance of a material may vary to some degree From one test to another, and as such the ranges provided above are based on testing using a method as described herein.

An applicator may comprise a material that is naturally occurring. Examples of naturally occurring materials suitable for use with an applicator provided by the present material include cotton. silk, or blends thereof refined to have a structural matrix able to meet the performance requirements for dose delivery. An applicator may comprise a synthetic material similarly with a structural matrix that enables holding a naloxone composition in a manner to enable release on to a surface that meets the performance requirements of dose delivery. Examples of synthetic material suitable for use for an applicator provided by the present disclosure include polyester, nylon, rayon, polyvinyl chloride, polyurethane, or blends thereof. An applicator may also comprise a material that blends or separately includes a naturally occurring and/or a synthetic material such as for example a cotton-rayon blend or for example an applicator that includes cotton and separately includes rayon (without the two being blended).

An applicator may comprise a material arranged in different configurations. Examples of arrangements of a suitable material include a sheet of material, a mesh such as a material comprising interwoven fabric, a foam, a reticulated material, a porous material or any combination of any of the foregoing.

A suitable applicator material can be compressible or collapsible. A suitable applicator material can have a compression set, for example, greater than 10%, greater than 20%, greater than 30%, greater than 40%, greater than 50%, greater than 60%, greater than 70%, greater than 80%, or greater than 90%. where compression set is determined according to ASTM D395. A suitable applicator material can have a compression set, for example, from 10% to 100%, from 10% to 90%, from 20% to 80%, or from 20% to 70%, where compression set is determined according to ASTM D395.

An applicator provided by the present disclosure can comprise a synthetic foam.

A suitable synthetic foam can comprise, for example, a thermoplastic or a thermoset.

Examples of suitable thermoplastic foams include polyurethane foams, polyester foams, and polypropylene foams.

A suitable applicator material can be sterilized such as for example using radiation and can be a sterilizable grade of a thermoplastic or thermoset material.

A suitable foam can be a reticulated foam, such as a reticulated polyurethane foam.

A suitable foam can be compressible.

A suitable foam can have a compression set, for example, greater than 10%, where compression set is determined according to ASTM D395. It can be useful to use a foam having a low compression set such that following compression and release of a pharmaceutical composition onto a surface such as a nasal mucosa, the foam does not expand upon release of the pressure to cause the foam to reabsorb the released pharmaceutical composition to an appreciable extent.

A suitable foam can be a collapsible foam.

In some embodiments, a naloxone composition is held entirely on at least one outer surface of an applicator. In some embodiments, a naloxone composition is held both on an outer surface of an applicator and on one or more layers of material beneath the outer surface of the applicator (i.e. one or more inner layers of the applicator). In some of these embodiments, such as where a naloxone composition is held both on an outer layer and one or more inner layers of an applicator, a naloxone composition can be equally distributed between the outer layer of the applicator and the at least one inner layer of the applicator. A naloxone composition can be distributed on the outer surface of an applicator with less than 50% (vol % or wt %) of the naloxone composition being held by one or more inner layers of the applicator. A naloxone composition can be mainly held by one or more inner layers of an applicator with less than 50% (vol % to wt %) of a naloxone composition being held on the outer surface of the applicator. In some embodiments, a first naloxone composition can be held on the outer surface of an applicator and a second composition, which can be a second naloxone composition, can be held by at least one material layer beneath the outer surface of the applicator. An outer surface of an applicator can be shaped so that the applicator includes multiple discrete surfaces, and in some of these embodiments each of the discrete multiple surfaces holds the same naloxone composition, and in some embodiments a first discrete outer surface holds a first naloxone composition and a second discrete outer surface holds a second composition, which can be a second naloxone composition. For example, in an embodiment in which an applicator has a three dimensional triangular shape such as a pyramidal shape, a first surface of the outer surface of the applicator can hold a first naloxone composition and a second surface of the outer layer of the applicator can hold a second composition, which can be a second naloxone composition.

The first composition and the second composition can be the same or different. The first composition and the second composition can comprise the same active pharmaceutical ingredient (API) or a different API. For example, both the first composition and the second composition can comprise naloxone. For example, either the first composition or the second composition can comprise naloxone and the second composition can comprise an API that exhibits synergistic therapeutic efficacy with naloxone and/or comprises a compound effective in enhancing absorption of naloxone from the nasal mucosa into the systemic circulation.

An applicator can comprise an absorbent material that holds the naloxone composition by absorbing it. The ability of an applicator to absorb can be measured in different ways. As one example. the ability of an applicator to absorb is determined by contacting the applicator with a known quantity of a naloxone composition, withdrawing the applicator from the naloxone composition, and measuring how much of the known quantity of the naloxone composition remains (i.e. how much was not absorbed by the applicator). This absorption can then be expressed as a percentage. The measurement can be in terms of weight and/or volume.

An example of a technique for measuring the ability of a material to absorb a naloxone composition is as follows: A volume of a naloxone composition such as 1 mL of the naloxone composition can be contained in a container and the applicator can be inserted into the container to contact the 1 mL of the naloxone composition. The applicator is then withdrawn so that the applicator no longer contacts the naloxone composition. The volume of the remaining naloxone composition within the contain can be determined. In this example, if 0.1 mL of the naloxone composition remains within the container, the applicator absorbed 0.9 mL of the naloxone composition. Expressed as a percentage, the applicator absorbed 90% of the naloxone composition. The same technique or a similar technique can be used to determine the ability of an applicator to absorb a solid or semi-solid material as well. The same measuring technique can also be used to determine other mechanisms for holding the naloxone composition to the applicator including adsorption, chemical binding (including covalent and ionic), electrostatic coupling, and/or magnetic coupling. It should be understood that there are numerous techniques for measuring the ability of a material to draw and retain a naloxone composition and in the following, when an absorption (or other mechanism) ability is expressed in terms of the percent amount of the naloxone composition that is absorbed (or held by other mechanism), it is measured using this technique or a similar technique for measuring absorption (or other mechanism for holding the compound).

An applicator provided by the present disclosure can be configured to retain, for example, from 50 µL to 35 µL of a naloxone composition.

A naloxone composition can comprise, for example, a concentration of naloxone hydrochloride from 20 mg/mL to 100 mg/mL such as from 30 mg/mL to 80 mg/mL, or from 40 mg/mL to 60 mg/mL, 0.05 wt % $Na_2EDTA$ (ethylenediaminetetraacetic acid), 0.10 wt % benzalkonium chloride (BKC), 10 mM citric acid. 0.15 wt % NaCl, and with a pH of 4.5 adjusted with either NaOH or HCl. Other suitable naloxone compositions can be used.

An applicator can be configured to hold 70 μL of a naloxone composition. An applicator can be configured to hold 80 μL of a naloxone composition. An applicator can be configured to hold 90 μL of a naloxone composition. An applicator can be configured to hold 100 μL of a naloxone composition. An applicator can be configured to hold 110 μL of a naloxone composition. An applicator can be configured to hold 120 μL of a naloxone composition. An applicator can be configured to hold 130 μL of a composition. An applicator can be configured to hold 140 μL of a naloxone composition. An applicator can be configured to hold 150 μL of a naloxone composition. An applicator can be configured to hold 160 μL of a naloxone composition. An applicator can be configured to hold 170 μL of a naloxone composition. An applicator can be configured to hold 180 μL of a naloxone composition. An applicator can be configured to hold 190 μL of a naloxone composition. An applicator can be configured to hold 200 μL of a naloxone composition. An applicator can be configured to hold 210 μL of a naloxone composition. An applicator can be configured to hold 220 μL of a naloxone composition. An applicator can be configured to hold 230 μL of a naloxone composition. An applicator can be configured to hold 240 μL of a naloxone composition. An applicator can be configured to hold 250 μL of a naloxone composition. An applicator can be configured to hold 260 μL of a naloxone composition. An applicator can be configured to hold 270 μL of a naloxone composition. An applicator can be configured to hold 280 μL of a naloxone composition. An applicator can be configured to hold 290 μL of a naloxone composition. An applicator can be configured to hold 300 μL of a naloxone composition. An applicator can be configured to hold 310 μL of a naloxone composition. An applicator can be configured to hold 320 μL of a naloxone composition. An applicator can be configured to hold 330 μL of a naloxone composition. An applicator can be configured to hold 340 μL of a naloxone composition. An applicator can be configured to hold 350 μL of a naloxone composition.

An applicator provided by the present disclosure can hold, for example. from 70 μL to 350 μL of a naloxone composition, from 100 μL to 300 μL, or from 150 μL to 250 μL of a naloxone composition. An applicator provided by the present disclosure can hold, for example, greater than 70 μL of a naloxone composition, greater than 100 μL, greater than 150 μL, greater than 200 μL, greater than 250 μL, or greater than 300 μL of a naloxone composition. An applicator provided by the present disclosure can hold, for example, less than 350 μL of a naloxone composition, less than 300 μL, less than 250 μL, less than 200 μL, less than 150 μL, or less than 100 μL of a naloxone composition.

An applicator can hold naloxone hydrochloride in the amount that is 0.1 mg to 100 mg. An applicator can hold naloxone hydrochloride in the amount that is 0.1 mg to 0.5 mg, 0.1 mg to 1 mg, 0.1 mg to 2.5 mg, 0.1 mg to 5 mg, 0.1 mg to 7.5 mg, 0.1 mg to 10 mg, 0.1 mg to 12.5 mg, 0.1 mg to 15 mg, 0.1 mg to 20 mg, 0.1 mg to 50 mg, 0.1 mg to 100 mg, 0.5 mg to 1 mg, 0.5 mg to 2.5 mg, 0.5 mg to 5 mg, 0.5 mg to 7.5 mg, 0.5 mg to 10 mg, 0.5 mg to 12.5 mg, 0.5 mg to 15 mg, 0.5 mg to 20 mg, 0.5 mg to 50 mg, 0.5 mg to 100 mg, 1 mg to 2.5 mg, 1 mg to 5 mg, 1 mg to 7.5 mg, 1 mg to 10 mg, 1 mg to 12.5 mg, 1 mg to 15 mg, 1 mg to 20 mg, 1 mg to 50 mg, 1 mg to 100 mg, 2.5 mg to 5 mg, 2.5 mg to 7.5 mg, 2.5 mg to 10 mg, 2.5 mg to 12.5 mg, 2.5 mg to 15 mg, 2.5 mg to 20 mg, 2.5 mg to 50 mg, 2.5 mg to 100 mg, 5 mg to 7.5 mg, 5 mg to 10 mg, 5 mg to 12.5 mg, 5 mg to 15 mg, 5 mg to 20 mg, 5 mg to 50 mg, 5 mg to 100 mg, 7.5 mg to 10 mg, 7.5 mg to 12.5 mg, 7.5 mg to 15 mg, 7.5 mg to 20 mg, 7.5 mg to 50 mg, 7.5 mg to 100 mg, 10 mg to 12.5 mg, 10 mg to 15 mg, 10 mg to 20 mg, 10 mg to 50 mg, 10 mg to 100 mg, 12.5 mg to 15 mg, 12.5 mg to 20 mg, 12.5 mg to 50 mg, 12.5 mg to 100 mg, 15 mg to 20 mg, 15 mg to 50 mg, 15 mg to 100 mg, 20 mg to 50 mg, 20 mg to 100 mg, or 50 mg to 100 mg.

An applicator can hold naloxone hydrochloride in the amount that is 0.1 mg, 0.5 mg, 1 mg, 2.5 mg, 5 mg, 7.5 mg, 10 mg, 12.5 mg, 15 mg, 20 mg, 50 mg, or 100 mg, An applicator can hold naloxone in the amount that is at least 0.1 mg, 0.5 mg, 1 mg, 2.5 mg, 5 mg, 7.5 mg, 10 mg, 12.5 mg, 15 mg, 20 mg, or 50 mg, An applicator can hold naloxone hydrochloride in the amount that is at most 0.5 mg, 1 mg, 2.5 mg, 5 mg, 7.5 mg, 10 mg, 12.5 mg, 15 mg, 20 mg, 50 mg, or 100 mg.

An applicator provided by the present disclosure can hold, for example, from 0.5 mg to 20 mg of naloxone hydrochloride, from 1 mg to 16 mg, from 1 mg to 12 mg, from 1 mg to 8 mg, from 1 mg to 6 mg, from 4 mg to 20 mg, from 6 mg to 18 mg, or from 8 mg to 16 mg of naloxone hydrochloride. An applicator provided by the present disclosure can hold, for example, greater than 0.5 mg of naloxone hydrochloride, greater than 2 mg, greater than 5 mg, greater than 10 mg, or greater than 15 mg of an API. An applicator provided by the present disclosure can hold, for example, less than 20 mg of an API, less than 15 mg, less than 10 mg, or less than 5 mg of naloxone hydrochloride.

An applicator can comprise a material configured to release a naloxone composition retained by the material when the applicator contacts a target surface. A device can be manually applied to a target surface to which the naloxone composition held by the applicator is to be delivered. For example, a device as described herein can be configured to be inserted into a nasal cavity of a patient. An applicator can be configured to release a composition onto the surface of a nasal mucosa. After the naloxone composition is released onto the nasal mucosa the naloxone composition can be absorbed through the nasal mucosa into the blood and circulatory system of the patient for either local or systemic or targeted therapy. For example. an applicator can release naloxone to a nasal mucosal surface of an individual when a device provided by the present disclosure is inserted into a nasal passage of an individual and the applicator releases the naloxone composition onto the nasal mucosa of the patient.

A naloxone composition can be released from an applicator with only light manually induced contact of the applicator against a target surface. A naloxone composition can be released from the applicator in response to the application of a force that pushes the applicator against the target surface. The naloxone composition can be released from an applicator in response to the rolling of the applicator against the target surface. An applicator can be squeezed manually or through the operation of the device so that the squeezing of the applicator releases a naloxone composition onto the target surface.

An example of a technique for measuring the ability of a material to release a naloxone composition is as follows: An applicator that is holding a known quantity of a naloxone composition is caused to release the naloxone composition. That is, depending on the mechanism of release (e.g. light contact, contact with pressure, rolling, or squeezing), the mechanism is applied to the applicator when the applicator is held against an absorbent material such as absorbent paper. The amount transferred to the absorbent material is then measured. The ability to release the naloxone composition is expressed as a percentage in comparison to the amount held on the applicator. For example, the applicator is known to hold 1 mL of a naloxone composition and is caused to release the naloxone composition on a surface of an absorbent material. In this example, if 0.9 mL of the composition is determined to be on the absorbent material, the ability of the applicator to release is expressed as 90%. It should be understood that numerous techniques exist for measuring the ability of a material to release a naloxone composition and in the following, when an ability to release is expressed in terms of the percent amount of the naloxone composition that is released, it is measured using this technique or a similar technique for measuring release of a naloxone composition.

Using the absorbent paper release test method described in Example 3, an applicator can be configured to release 100% of naloxone hydrochloride initially retained by the applicator, wherein the amount of naloxone hydrochloride released is determined using gravimetric analysis. An applicator can be configured to release 99.9% of naloxone hydrochloride. An applicator can be configured to release 99.8% of naloxone hydrochloride. An applicator can be configured to release 99.7% of naloxone hydrochloride. An applicator can be configured to release 99.6% of naloxone hydrochloride. An applicator can be configured to release 99.5% of naloxone hydrochloride. An applicator can be configured to release 99.4% of naloxone hydrochloride. An applicator can be configured to release 99.3% of naloxone hydrochloride. An applicator can be configured to release 99.2% of naloxone hydrochloride. An applicator can be configured to release 99.1% of naloxone hydrochloride. An applicator can be configured to release 99% of naloxone hydrochloride. An applicator can be configured to release 98.9% of naloxone hydrochloride. An applicator can be configured to release 98.8% of naloxone hydrochloride. An applicator can be configured to release 98.7% of naloxone hydrochloride. An applicator can be configured to release 98.6% of naloxone hydrochloride. An applicator can be configured to release 98.5% of naloxone hydrochloride. An applicator can be configured to release 98.4% of naloxone hydrochloride. An applicator can be configured to release 98.3% of naloxone hydrochloride. An applicator can be configured to release 98.2% of naloxone hydrochloride. An applicator can be configured to release 98.1% of naloxone hydrochloride. An applicator can be configured to release 98% of naloxone hydrochloride. An applicator can be configured to release 97% of naloxone hydrochloride. An applicator can be configured to release 96% of naloxone hydrochloride. An applicator can be configured to release 95% of naloxone hydrochloride. An applicator can be configured to release 94% of naloxone hydrochloride. An applicator can be configured to release 93% of naloxone hydrochloride. An applicator can be configured to release 92% of naloxone hydrochloride. An applicator can be configured to release 91% of naloxone hydrochloride. An applicator can be configured to release 90% of naloxone hydrochloride. An applicator can be configured to release 89% of naloxone hydrochloride. An applicator can be configured to release 88% of naloxone hydrochloride. An applicator can be configured to release 87% of naloxone hydrochloride. An applicator can be configured to release 86% of naloxone hydrochloride. An applicator can be configured to release 85% of naloxone hydrochloride. An applicator can be configured to release 84% of naloxone hydrochloride. An applicator can be configured to release 83% of naloxone hydrochloride. An applicator can be configured to release 82% of naloxone hydrochloride. An applicator can be configured to release 81% of naloxone hydrochloride. An applicator can be configured to release 80% of naloxone hydrochloride. An applicator can be configured to release from 80% and 100% of naloxone hydrochloride. The amount released from the applicator is determined using the absorbent paper method described herein. The percent (%) release can refer to wt %.

An applicator provided by the present disclosure can be configured, for example, to release from 10 wt % to 100 wt % of naloxone hydrochloride and a naloxone composition during a single use, from 10 wt %, to 90 wt %, from 10 wt % to 80 wt %, from 10 wt % to 60 wt %, from 10 wt % to 40 wt %, from 20 wt %, to 90 wt %, from 20 wt % to 80 wt %, from 20 wt % to 60 wt %, from 20 wt % to 40 wt %, from 40 wt % to 90 wt %, from 40 wt % to 80 wt %, from 40 wt % to 60 wt %, from 50 wt % to 90 wt %, or from 60 wt % to 90 wt % of naloxone hydrochloride and a naloxone composition during a single use, where wt % is based on the weight of the naloxone hydrochloride or naloxone composition initially retained by the applicator before use.

An applicator provided by the present disclosure can be configured, for example, to release greater than 20 wt % of naloxone hydrochloride and a naloxone composition during a single use, greater than 30 wt %, greater than 40 wt %, greater than 50 wt %, greater than 60 wt %, greater than 70 wt %, greater than 80 wt %, or greater than 90 wt % of naloxone hydrochloride and a naloxone composition. An applicator provided by the present disclosure can be configured, for example, to release from 20 wt % to 100 wt % of naloxone hydrochloride and a naloxone composition during a single use, where wt % is based on the weight of naloxone hydrochloride or a naloxone composition initially retained by the applicator before use.

An applicator provided by the present disclosure can be configured, for example, to release from 20 vol % to 100 vol % of a naloxone composition during a single use, from 20 vol %, to 90 vol %, from 20 vol % to 80 vol %, from 20 vol % to 60 vol %, from 20 vol % to 40 vol %, from 40 vol % to 90 vol %, from 40 vol % to 80 vol %, from 40 vol % to 60 vol %, from 50 vol % to 90 vol %, or from 60 vol % to 90 vol % of a naloxone composition during a single use, where vol % is based on the volume of the naloxone composition initially retained by the applicator before use.

An applicator provided by the present disclosure can be configured, for example, to release greater than 20 vol % of a naloxone composition during a single use, greater than 30 vol %, greater than 40 vol %, greater than 50 vol %, greater than 60 vol %, greater than 70 vol %, greater than 80 vol %, or greater than 90 vol % of a naloxone composition. An applicator provided by the present disclosure can be configured, for example, to release from 20 vol % to 100 vol % of a naloxone composition during a single use, where vol % is based on the volume of the naloxone composition initially retained by the applicator before use.

In some embodiments, an applicator provided by the present disclosure can be configured to release a composition during a single use in an amount that is reproducible. For example, the relative standard deviation (RSD) of naloxone hydrochloride released in a single use of an applicator can be less than 10%, less than 8%, less than 6%, or less than 4%, where the RSD is determined using the absorbent paper method described in Example 3.

An applicator can be configured to release 70 µL of a naloxone composition during a single use. An applicator can be configured to release 80 µL of a naloxone composition during a single use. An applicator can be configured to release 90 µL of a naloxone composition during a single use. An applicator can be configured to release 100 µL of a naloxone composition during a single use. An applicator can be configured to release 110 µL of a naloxone composition during a single use. An applicator can be configured to release 120 µL of a naloxone composition during a single use. An applicator can be configured to release 130 µL of a naloxone composition during a single use. An applicator can be configured to release 140 µL of a naloxone composition during a single use. An applicator can be configured to release 150 µL of a naloxone composition during a single use. An applicator can be configured to release 160 µL of a naloxone composition during a single use. An applicator can be configured to release 170 µL of a naloxone composition during a single use. An applicator can be configured to release 180 µL of a naloxone composition during a single use. An applicator can be configured to release 190 µL of a naloxone composition during a single use. An applicator can be configured to release 200 µL of a naloxone composition during a single use. An applicator can be configured to release 210 µL of a naloxone composition during a single use. An applicator can be configured to release 220 µL of a naloxone composition during a single use. An applicator can be configured to release 230 µL of a naloxone composition during a single use. An applicator can be configured to release 240 µL of a naloxone composition during a single use. An applicator can be configured to release 250 µL of a naloxone composition during a single use. An applicator can be configured to release 260 µL of a naloxone composition during a single use. An applicator can be configured to release 270 µL of a naloxone composition during a single use. An applicator can be configured to release 280 µL of a naloxone composition during a single use. An applicator can be configured to release 290 µL of a naloxone composition during a single use. An applicator can be configured to release 300 µL of a naloxone composition during a single use. An applicator can be configured to release 310 µL of a naloxone composition during a single use. An applicator can be configured to release 320 µL of a naloxone composition during a single use. An applicator can be configured to release 330 µL of a naloxone composition during a single use. An applicator can be configured to release 340 µL of a naloxone composition during a single use. An applicator can be configured to release 350 µL of a naloxone composition during a single use.

An applicator provided by the present disclosure can be configured to release, for example, from 50 µL to 350 µL of a naloxone composition during a single use, from 100 µL to 300 µL, from 100 µL to 250 µL, from 100 µL to 200 µL, from 150 µL to 350 µL, from 150 µL to 300 µL, from 150 µL to 250 µL, or from 200 µL to 35 µL of a naloxone composition during a single use.

An applicator provided by the present disclosure can be configured to release. for example, greater than 50 µL of a naloxone composition during a single use, greater than 100 µL, greater than 150 µL, greater than 200 µL, greater than 250 µL, or greater than 300 µL of a naloxone composition during a single use.

An applicator can release naloxone hydrochloride in the amount that is 0.1 mg to 100 mg during a single use. An applicator can release naloxone hydrochloride in the amount that is 0.1 mg to 0.5 mg during a single use. 0.1 mg to 1 mg, 0.1 mg to 2.5 mg, 0.1 mg to 5 mg, 0.1 mg to 7.5 mg, 0.1 mg to 10 mg, 0.1 mg to 12.5 mg, 0.1 mg to 15 mg, 0.1 mg to 20 mg, 0.1 mg to 50 mg, 0.1 mg to 100 mg, 0.5 mg to 1 mg, 0.5 mg to 2.5 mg, 0.5 mg to 5 mg, 0.5 mg to 7.5 mg, 0.5 mg to 10 mg, 0.5 mg to 12.5 mg, 0.5 mg to 15 mg, 0.5 mg to 20 mg, 0.5 mg to 50 mg, 0.5 mg to 100 mg, 1 mg to 2.5 mg, 1 mg to 5 mg, 1 mg to 7.5 mg, 1 mg to 10 mg, 1 mg to 12.5 mg, 1 mg to 15 mg, 1 mg to 20 mg, 1 mg to 50 mg, 1 mg to 100 mg, 2.5 mg to 5 mg, 2.5 mg to 7.5 mg, 2.5 mg to 10 mg, 2.5 mg to 12.5 mg, 2.5 mg to 15 mg, 2.5 mg to 20 mg, 2.5 mg to 50 mg, 2.5 mg to 100 mg, 5 mg to 7.5 mg, 5 mg to 10 mg, 5 mg to 12.5 mg, 5 mg to 15 mg, 5 mg to 20 mg, 5 mg to 50 mg, 5 mg to 100 mg, 7.5 mg to 10 mg, 7.5 mg to 12.5 mg, 7.5 mg to 15 mg, 7.5 mg to 20 mg, 7.5 mg to 50 mg, 7.5 mg to 100 mg, 10 mg to 12.5 mg, 10 mg to 15 mg, 10 mg to 20 mg, 10 mg to 50 mg, 10 mg to 100 mg, 12.5 mg to 15 mg, 12.5 mg to 20 mg, 12.5 mg to 50 mg, 12.5 mg to 100 mg, 15 mg to 20 mg, 15 mg to 50 mg, 15 mg to 100 mg, 20 mg to 50 mg, 20 mg to 100 mg, or 50 mg to 100 mg.

An applicator can release naloxone hydrochloride during a single use the amount that is 0.1 mg, 0.5 mg, 1 mg. 2.5 mg, 5 mg, 7.5 mg, 10 mg, 12.5 mg, 15 mg, 20 mg, 50 mg, or 100 mg. An applicator can release naloxone in the amount that is at least 0.1 mg. 0.5 mg, 1 mg. 2.5 mg, 5 mg, 7.5 mg, 10 mg, 12.5 mg, 15 mg, 20 mg, or 50 mg. An applicator can release naloxone hydrochloride during a single use in the amount that is at most 0.5 mg, 1 mg, 2.5 mg, 5 mg. 7.5 mg, 10 mg, 12.5 mg, 15 mg, 20 mg, 50 mg, or 100 mg.

An applicator provided by the present disclosure can release, for example, from 0.1 mg to 100 mg of naloxone hydrochloride during a single use, from 0.1 mg to 80 mg, from 0.1 mg to 60 mg, from 0.1 mg to 40 mg, or from 0.1 mg to 20 mg, of naloxone hydrochloride during a single use.

An applicator provided by the present disclosure can release, for example, greater than 0.1 mg of naloxone hydrochloride during a single use, greater than 1 mg, greater than 5 mg, greater than 10 mg, greater than 15 mg, greater than 20 mg, greater than 40 mg, greater than 60 mg, or greater than 80 mg of naloxone hydrochloride during a single use.

An applicator provided by the present disclosure can release, for example, from 1 mg to 30 mg of naloxone hydrochloride during a single use, from 1 mg to 25 mg, from 1 mg to 20 mg, from 1 mg to 15 mg, from 1 mg to 10 mg, from 1 mg to 5 mg, from 5 mg to 25 mg, from 5 mg to 20 mg, or from 5 mg to 15 mg of naloxone hydrochloride during a single use.

A device provided by the present disclosure comprises a handle that is coupled to an applicator. The handle is configured so that a user can manually direct the applicator to a target site of the nasal mucosa by holding the handle and manually moving the applicator. A handle is configured so that a pressure applied by the user to the handle is transmitted to the applicator. In some embodiments, a handle can be configured with respect to its dimensions such as having a relatively small diameter and relatively long length, to facilitate rotation of the applicator.

A handle can be formed of a plastic material such as polypropylene or polyethylene, but as will be understood nearly any rigid and light material is suitable for use in forming a handle.

A handle can comprise a sterilizable polymer.

A device can further include a stop that is configured to direct the applicator to a desired position within the nasal cavity and to prevent the applicator from being advanced beyond a target area of the nasal cavity. A stop can comprise a skirt positioned essentially perpendicular to the handle, a post essentially perpendicular to the handle, or a protrusion from the handle. A stop can be positioned along the handle at a position that will situate the applicator proximate the middle turbinate and/or the inferior turbinate. This is achieved by having the stop having a dimension perpendicular to the axis of the handle that is wider than the nasal opening. As the applicator is inserted into the nasal opening, at some point the stop contacts the outside of the nostril surrounding the nasal opening and prevents the applicator from advancing further into the nasal cavity, and thereby situates the applicator proximate the middle turbinate and/or the inferior turbinate. A stop can have any suitable shape and dimensions configured to situate the applicator proximate the middle turbinate and/or the inferior turbinate when the applicator is inserted into the nasal cavity. For example, the stop can be shaped as a disk, a bar, a sphere, a cone, or a one or two-dimensional.

An applicator of the device can be covered with a cap that covers and protects the applicator. In these embodiments, a naloxone composition is retained by the applicator (i.e. is held by the applicator) and the cover surrounds the applicator so as to aid in retention of the naloxone composition and to protect the applicator from physical damage. The cap can be made of any suitable material. For example, the cap can be made of a plastic such as polyethylene or polypropylene. The cap can have any suitable shape or dimension such that the cap can be inserted over the applicator and can be easily removed during use. For example, a cap can be in the shape of a sleeve.

A device can be used for delivery of naloxone hydrochloride and prior to use the device can be partially or completely enveloped to keep the device sanitary and, in some embodiments, sterile.

During storage and before use a device provided by the parent disclosure can be retained by a package. For example, the package can comprise a foil envelope or a thermoformed tray with a foil seal. The seal can provide a moisture barrier.

Figure 2A:
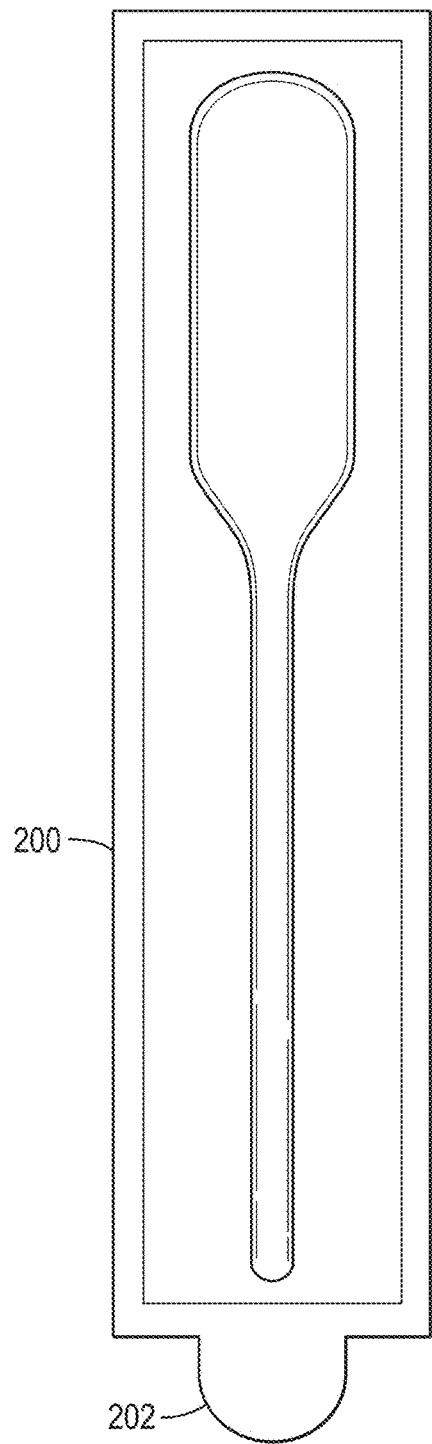
FIGS. 2A and 2B show an example of a foil envelope 200 enclosing a device provided by the present disclosure.
Figure 2B:
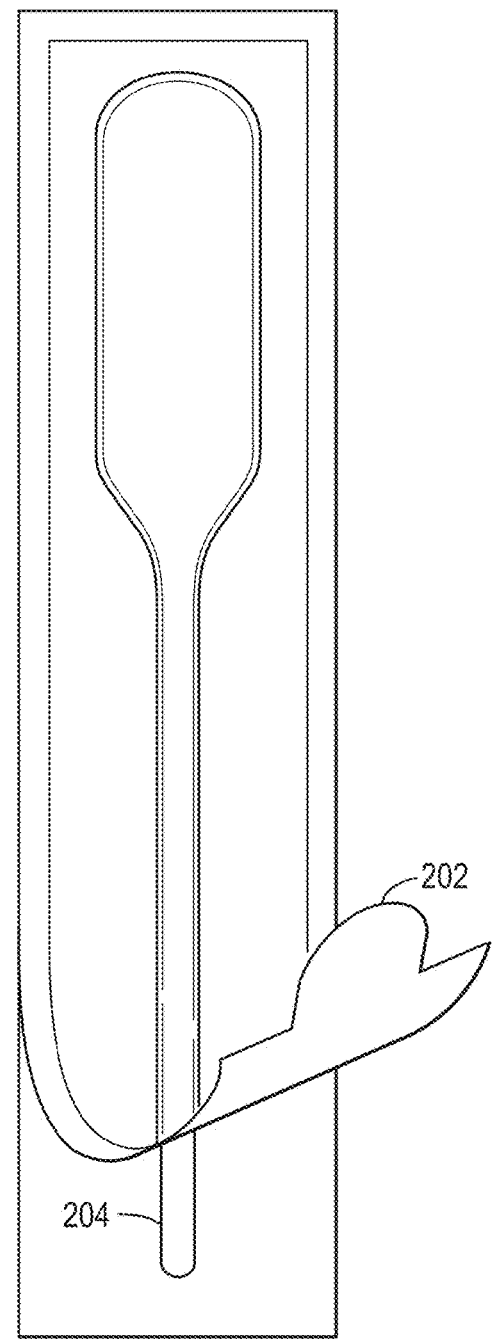

FIGS. 2A and 2B show an example of a package comprising a foil envelope 200 enclosing a device provided by the present disclosure. Such a foil envelope 200 may include a mechanism to aid in releasing the device such as a pull tab 202. FIG. 2B shows a pull tab 202 pulled back to reveal device handle 204 which when pulled removes the device from the foil envelope 200.

An applicator provided by the present disclosure can comprise a polyurethane material. In such embodiment, the polyurethane may be substantially homogeneous in composition and can be a foam. However, various compositions (including non-homogenous) and arrangements are suitable with respect to use of polyurethane material with the device applicator.

An applicator can comprise reticulated polyurethane foam. The reticulated polyurethane foam can have a pore count, for example, from 60 pores/inch to 100 pores/inch and a pore size of 0.01 inches to 0.0167 inches (254 μm to 424 μm). The reticulated polyurethane can have a density of from 1.7 lb/ft$^3$ to 2.5 lb/ft$^3$ (27 kg/m$^3$ to 40.0 kg/m$^3$) such as from 1.9 lb/ft$^3$ to 2.3 lb/ft$^3$ (30.5 kg/m$^3$ to 36.8 kg/m$^3$) to where density is determined according to ASTM D3575.

An applicator can comprise polyurethane, wherein the applicator can have a diameter of 8 mm and a length of 22 mm. An applicator can have a diameter of 6 mm, can have a diameter of 7 mm, can have a diameter of 8 mm, can have a diameter of 9 mm. An applicator can have a diameter of 10 mm. An applicator can have a diameter of 11 mm. An applicator can have a diameter of 12 mm. An applicator can have a diameter of 13 mm. An applicator can have a diameter of 14 mm. An applicator can have a diameter of 15 mm, can have a diameter of 16 mm, can have a length of 12 mm. An applicator can have a length of 13 mm. An applicator can have a length of 14 mm. An applicator can have a length of 15 mm. An applicator can have a length of 16 mm. An applicator can have a length of 17 mm. An applicator can have a length of 18 mm. An applicator can have a length of 19 mm. An applicator can have a length of 20 mm. An applicator can have a length of 21 mm. An applicator can have a length of 22 mm. An applicator can have a length of 23 mm. An applicator can have a length of 24 mm. An applicator can have a length of 25 mm. An applicator can have a length of 26 mm. An applicator can have a length of 27 mm. An applicator can have a length of 28 mm. An applicator can have a length of 29 mm. An applicator can have a length of 30 mm. An applicator can have a length of 31 mm. An applicator can have a length of 32 mm, can have a diameter of 6 to 12 mm and a length of 12 to 30 mm.

An applicator provided by the present disclosure can have a diameter, for example, from 5 mm to 25 mm, from 7 mm to 23 mm, from 9 mm to 21 mm, or from 11 mm to 19 mm. An applicator can have a diameter for example, greater than 5 mm, greater than 10 mm, greater than 15 mm, or greater than 20 mm. An applicator can have a diameter, for example, less than 25 mm, less than 20 mm, less than 15 mm, or less than 10 mm. The diameter refers to the dimension of the applicator perpendicular to the long axis of the handle.

An applicator can have a length from 10 mm to 30 mm, from 12 mm to 28 mm, from 14 mm to 26 mm, or from 16 mm to 24 mm. An applicator can have a length, for example, greater than 10 mm, greater than 15 mm, greater than 20 mm, or greater than 25 mm. An applicator can have a length, for example, less than 30 mm, less than 25 mm, less than 20 mm, less than 15 mm, or less than 10 mm. The length refers to the dimension parallel to the long axis of the handle.

An applicator can have a volume, for example, from 0.055 in$^3$ to 0.075 in$^3$ such as from 0.6 in$^3$ to 0.07 in$^3$. An applicator can have a volume, for example, from 500 mm$^3$ to 1,500 mm$^3$ such as from 750 mm$^3$ to 1.250 mm$^3$. The volume of an applicator refers to the volume based on the external dimensions of the applicator as a solid body. The applicator can include internal voids.

A device provided by the present disclosure can be included in a kit that may be used to administer the naloxone composition to a patient for therapeutic purposes. A kit can include a packaged device suitable for administering naloxone hydrochloride to a patient and instructions for administering the naloxone composition to the patient. A kit for use in treating an opioid overdose of a patient can comprise a packaged device provided by the present disclosure and instructions for using the device for administering the naloxone composition to the nasal mucosa of a patient having an opioid overdose. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Methods provided by the present disclosure comprise using a device provided by the present disclosure for administering naloxone hydrochloride to a patient for treating an opioid overdose. In some embodiments. a method as described herein is carried out by the individual who is in need of the compound (i.e. self-administration). In some embodiments, the method is carried out by an individual who is not the individual in need of the compound (i.e. administration by another). For example, in some embodiments, a device provided by the present disclosure is used by a first individual to deliver a compound to a second individual who is incapacitated or otherwise unable to self-administer the compound to themselves using the device.

Figure 3:
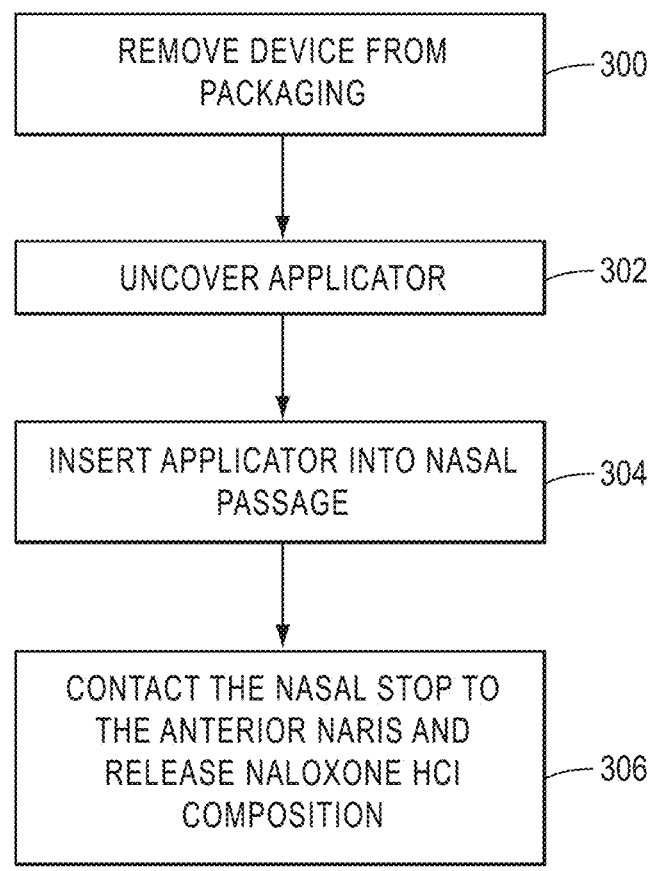
FIG. 3 shows an example of a method for using a device provided by the present disclosure to deliver naloxone hydrochloride to an individual.

FIG. 3 shows an example of method for using a device provided by the present disclosure to naloxone hydrochloride to an individual having an opioid overdose. As described above, in some embodiments, a device provided by the present disclosure can include an applicator comprising polyurethane. The polyurethane applicator can have a pore count from 60 to 100 pores per inch, pore size of 0.01 in to 0.0167 in (0.25 mm to 0.42 mm) and, in some embodiments, a density of from 1.7 lb/ft$^3$ to 2.5 lb/ft$^3$ (27 kg/m$^3$ to 40.0 kg/m$^3$). Further, in some embodiments, a polyurethane applicator holds between any amount of compound containing composition from 70 µL to 350 µL. A device provided by the present disclosure can further include a handle used to manually move the applicator. In an optional step 300, in embodiments that include a packaging, a device as described herein is removed from a packaging. A packaging may be, for example, a foil envelope that either wholly or partially covers the device. In an optional step 302, in embodiments including a cap, the cap is removed thereby uncovering the device. In a step 304, using the handle, a user manually inserts the device into a body orifice such as, for example, a nasal passage. In this step, in some embodiments, a stop prevents the applicator from advancing too far into the orifice. In a step 306, the applicator is delivered to a target tissue surface such as, for example, a nasal mucosa. In some embodiments, in this step, the applicator contacts the target tissue surface which causes release of the naloxone composition held by the applicator onto the target tissue surface. In some embodiments, a force is applied to the applicator to press it against the target tissue surface in order to cause release of the naloxone composition onto the target tissue surface. In some embodiments, the applicator is rolled (by turning the handle of the device) against the target tissue surface in order to cause release of the naloxone composition onto the target tissue surface. In some embodiments, after an applicator is positioned near a target tissue, the target tissue surface is pressed against the applicator resulting in release of the naloxone composition held by the applicator. For example, in an embodiment where an applicator is positioned near a nasal mucosa within a nasal passage, the side of the nose or nostril is manually pressed against the applicator resulting in release of the naloxone composition from the applicator.

In some embodiments, the method provided by the present disclosure is carried out only a single time. That is, the method is configured so that a sufficient amount of naloxone hydrochloride is delivered to an individual using the method a single time. For example, use of the method described herein for delivery of naloxone to an individual experiencing an opioid overdose delivers a dose of the naloxone to the individual that is sufficient to treat the opioid overdose in a single use of the method (i.e. via a single application of the applicator to the nasal mucosa). In some of these embodiments, the amount of naloxone hydrochloride released from the applicator is at least 1 mg of naloxone hydrochloride, such as at least 2 mg, at least 4 mg, at least 6 mg, or at least 8 mg of naloxone hydrochloride from the applicator. In some embodiments, use of the method described herein results in release of 4 mg of naloxone hydrochloride from the applicator. Use of the method can result in release of 5 mg of naloxone from the applicator. Use of the method can result in release of 6 mg of naloxone from the applicator. Use of the method can result in release of 7 mg of naloxone from the applicator. Use of the method can result in release of 8 mg of naloxone from the applicator. Use of the method can result in release of 9 mg of naloxone from the applicator. Use of the method can result in release of 10 mg of naloxone from the applicator. Use of the method can result in release of 11 mg of naloxone from the applicator. Use of the method can result in release of 12 mg of naloxone from the applicator. Use of the method can result in release of 13 mg of naloxone from the applicator. Use of the method can result in release of 14 mg of naloxone from the applicator. Use of the method can result in release of 15 mg of naloxone from the applicator. Use of the method can result in release of 16 mg of naloxone from the applicator. Use of the method can result in release of 17 mg of naloxone from the applicator. Use of the method can result in release of 18 mg of naloxone from the applicator. Use of the method can result in release of 19 mg of naloxone from the applicator. In some embodiments, use of the method described herein results in release of 20 mg of naloxone from the applicator.

Use of a method provided by the present disclosure can release, for example, from 4 mg to 20 mg of naloxone hydrochloride from the applicator, from 6 mg to 18 mg, from 8 mg to 16 mg, or from 10 mg to 14 mg of naloxone from the applicator. Use of a method provided by the present disclosure can release, for example, greater than 4 mg naloxone hydrochloride, greater than 6 mg, greater than 8 mg, greater than 10 mg, greater than 12, mg, greater than 14 mg, greater than 16 mg, or greater than 18 mg of naloxone hydrochloride from the applicator. Use of a method provided by the present disclosure can release, for example, less than 20 mg naloxone hydrochloride, less than 18 mg, less than 16 mg, less than 14 mg, less than 12 mg, less than 10 mg, less than 8 mg or less than 6 mg naloxone hydrochloride from the applicator.

A device provided by the present disclosure can be used to administer naloxone hydrochloride to the nasal mucosa. A device provided by the present disclosure can be used to administer naloxone hydrochloride to the nasal mucosa of the middle turbinate and/or inferior turbinate.

Methods provided by the present disclosure can comprise having the patient breathe through the mouth and not the nose, having the patient lie supine (face up) or on their side, inserting an applicator into a nostril until the stop rests against the anterior naris, placing a finger and thumb on either side of the nose and squeezing the nostrils firmly closed for from 3 seconds to 6 seconds, and withdrawing the applicator. As an alternative, the nostrils can remain firmly squeezed while the applicator is withdrawn from the nasal cavity.

Following administration to a population of patients the method provides a naloxone plasma pharmacokinetic profile characterized by $T_{max}$ less than 0.3 (±10%) hour and a $C_{max}$ from 4,400 (±10%) pg/mL to 6,600 (±10%) pg/mL, wherein the applicator initially retains 12 mg of naloxone HCl in composition comprising 60 mg/mL naloxone hydrochloride. For example, a $T_{max}$ less than 0.3 (±10%) h means that the $T_{max}$ can be less than 0.27 h to less than 0.33 h, such as, for example, less than 0.27 h, less than 0.29 h, less than 0.31 h or less than 0.33 h.

Following administration of from 4.0 mg to 5.0 mg of naloxone hydrochloride to a population of patients. the naloxone plasma pharmacokinetic profile is bioequivalent to a pharmacokinetic profile characterized by a $C_{max}$ of 5,700 (±10%) pg/mL, a $T_{max}$ of 0.26 (±10%) h, and a $AUC_{last}$ of 8,000(±10%) pg×hr/mL, wherein the applicator initially retains 12 mg of naloxone HCl in composition comprising 60 mg/mL naloxone hydrochloride.

Following administration of from 4.0 mg to 5.0 mg of naloxone hydrochloride to a population of patients, the naloxone plasma pharmacokinetic profile is further characterized by a pAUC at 5 min of 446 (±10%) pg×hr/mL, and a pAUC at 15 min of 834 (±10%) pg×hr/mL, wherein the applicator initially retains 12 mg of naloxone HCl in composition comprising 60 mg/mL naloxone hydrochloride.

Following administration of from 4.0 mg to 5.0 mg of naloxone to a population of patients, the naloxone plasma pharmacokinetic profile is characterized by a $T_{1/2}$ of 2.3 (±10%) hours wherein the applicator initially retains 12 mg of naloxone HCl in composition comprising 60 mg/mL naloxone hydrochloride.

Following administration of from 4.0 mg to 5.0 mg of naloxone to a population of patients, the naloxone plasma pharmacokinetic profile is characterized by a pAUC at 30 min of 3,511 (±10%) pg×hr/mL wherein the applicator initially retains 12 mg of naloxone HCl in composition comprising 60 mg/mL naloxone hydrochloride.

Figure 9:
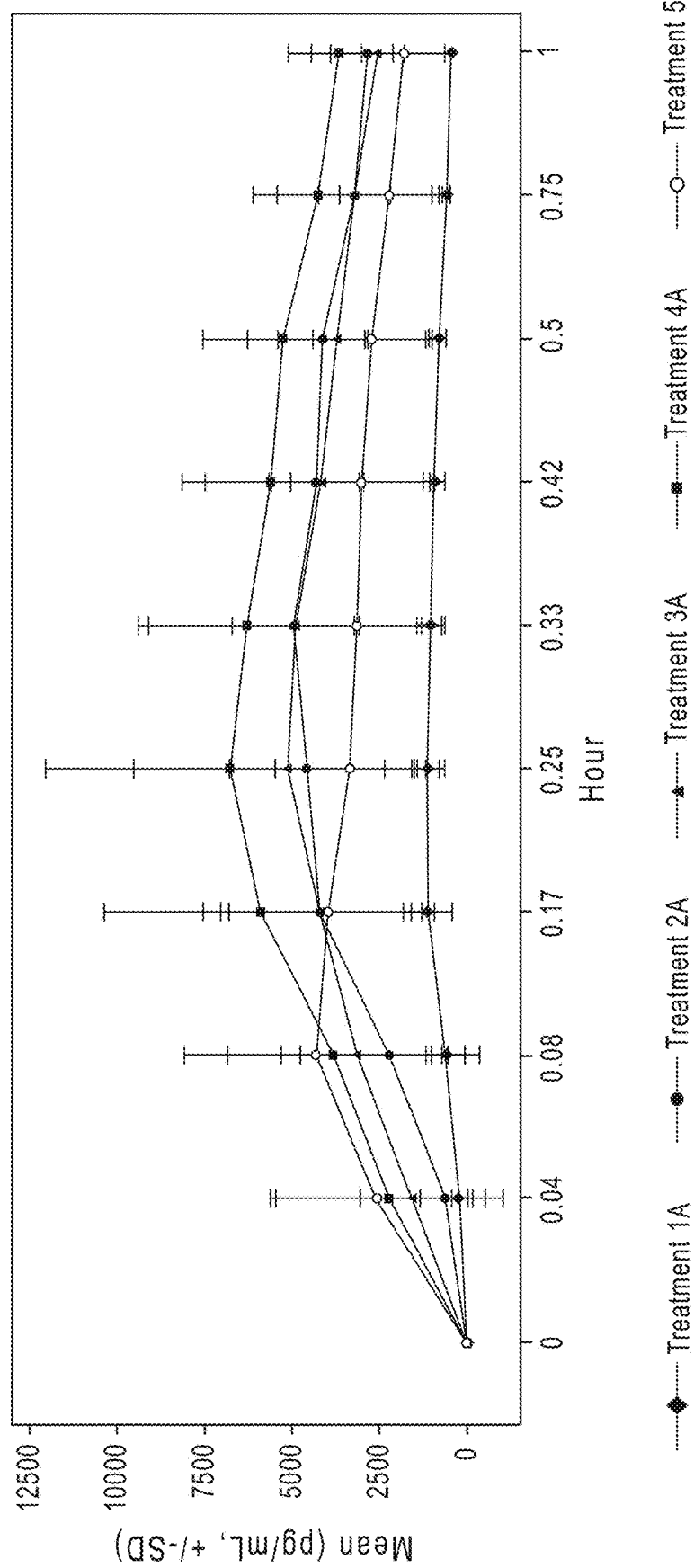
FIG. 9 shows the plasma naloxone pharmacokinetic profile during the first hour following administration of a naloxone composition using different administration methods.
Figure 10:
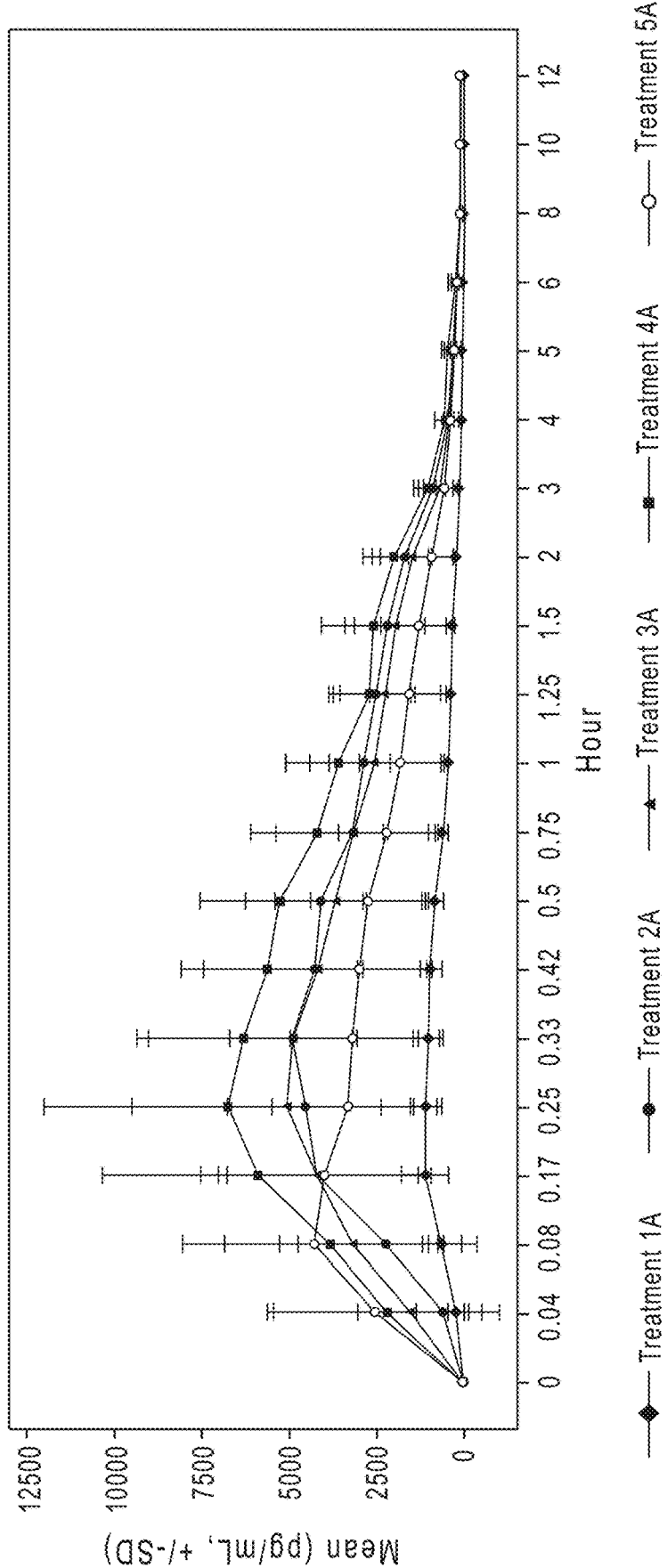
FIG. 10 shows the plasma naloxone pharmacokinetic profile during the first 12 hours following administration of a naloxone composition using different administration methods.

Following administration of a dose of naloxone HCl as a composition having a naloxone HCL concentration of 60 mg/mL to a population of patients, the plasma naloxone PK profile can be bioequivalent to the plasma naloxone PK profile for any one of Treatment 3A, Treatment 4A, or Treatment 5A as shown in FIGS. 9 and 10.

A single dose of 4 mg naloxone hydrochloride administered using a device and method provided by the present disclosure, when administered to a population of patients, can exhibit a naloxone plasma pharmacokinetic profile that is bioequivalent to the pharmacokinetic profile for Treatment 3A as shown in FIGS. 9 and 10, and/or can exhibit the bioequivalent pharmacokinetic parameters to those summarized for Treatment 3A in Table 12.

A single dose of 4 mg naloxone hydrochloride administered using a device and method provided by the present disclosure, when administered to a population of patients can exhibit a $T_{max}$ from 0.23 h to 0.29 h such as from 0.24 h to 0.28 h; a $C_{max}$ from 5,129 pg/mL to 6,288 pg/mL such as from 5,414 pg/mL to 5,983 pg/mL; a pAUC30 from 400 pg×h/mL to 489 pg×h/mL such as from 423 pg×h/mL to 467 pg×h/mL; an $AUC_{last}$ from 7,192 pg×h/mL to 8,791 pg×h/mL such as from 7,552 pg×h/mL to 8,391 pg×h/mL; and/or a $T_{1/2}$ from 2.1 h to 2.8 h such as from 2.2 h to 2.5 h.

For comparison, the naloxone plasma PK profile following nasal administration of a 4 mg dose of naloxone via a nasal spray is characterized by a $T_{max}$ of 0.50 hours, a $C_{max}$ of 4.83 ng/ml, an $AUC_{last}$ of 7.95 ng×h/mL, and a $T_{1/2}$ of 2.08 h.

Naloxone is approved by the FDA for the treatment of an opioid overdose.

Methods for administering naloxone hydrochloride to the nasal mucosa provided by the present disclosure can be used to treat an opioid overdose that can be treated by administering naloxone hydrochloride.

Methods provided by the present disclosure for intranasally administering naloxone hydrochloride can be used to treat an opioid overdose.

Methods provided by the present disclosure for intranasally administering naloxone hydrochloride can be used to treat an opioid overdose, where the opioid overdose is associated with buprenorphine, carfentanil, codeine, fentanyl, hydrocodone, hydromorphone, meperidine, methadone, morphine, opium, oxycodone, oxymorphone, tramadol, or a combination of any of the foregoing.

A method provided by the present disclosure can comprise administering to a patient having an opioid overdose a therapeutically effective amount of naloxone hydrochloride for treating the opioid overdoes.

ASPECTS

The invention is further defined by the following aspects.

Aspect 1. A device for delivering naloxone to a nasal passage of an individual comprising: (a) an applicator with a polyurethane swab; (b) 70 to 350 μL of a liquid composition containing the naloxone that is held by the polyurethane swab; (c) a handle attached to the applicator; and wherein the polyurethane swab has a pore count from 60 to 100 pores per inch, pore size of 0.01 to 0.0167 inches and a density of from 1.7 to 2.3 pounds per cubic foot; wherein the applicator is configured to release a 4 mg to 20 mg dose of naloxone with a relative standard deviation less than 6% with a single use of the device.

Aspect 2. The device of aspect 1, wherein the polyurethane is reticulated.

Aspect 3. The device of aspect 1, wherein the liquid composition containing the naloxone comprises 60 mg/ml of naloxone.

Aspect 4. The device of aspect 1, wherein the polyurethane swab has a diameter from 6 mm to 12 mm and a length from 12 mm to 30 mm.

Aspect 5. The device of aspect 1, wherein the device includes a stop that is attached to the handle and prevents the applicator from advancing into the nasal passage when the stop contacts a nostril of the individual.

Aspect 6. The device of aspect 1, wherein the device is at least partially enclosed in a secondary container closure system.

Aspect 7. The device of aspect 1, wherein the liquid composition maintains stability and a shelf life of at least one year.

Aspect 8. A method for delivering naloxone to a nasal passage of an individual in need thereof, comprising: (a) receiving a device having an applicator and a handle, wherein the applicator comprises a polyurethane swab that holds 70 to 350 μL of a liquid composition containing the naloxone; (b) inserting the device into a nasal passage of the individual; and (c) releasing the liquid composition containing the naloxone onto a nasal mucosa of the individual by contacting the nasal mucosa of the individual with the applicator.

Aspect 9. The method of aspect 7, wherein the polyurethane swab has a pore size from 60 to 100 pores per inch, pore size of 0.01 to 0.0167 inches and a density of from 1.7 to 2.3 pounds per cubic foot.

Aspect 10. The method of aspect 7, wherein the polyurethane is reticulated.

Aspect 11. The method of aspect 7, wherein the liquid composition containing the naloxone comprises 60 mg/ml of naloxone.

Aspect 12. The method of aspect 7, wherein releasing the liquid composition onto the nasal mucosa of the individual results in release of a 4 mg to 20 mg dose of naloxone with a relative standard deviation less than 6% from the applicator.

Aspect 13. The method of aspect 7, wherein the device includes a stop that is attached to the handle and prevents the applicator from advancing into the nasal passage when the stop contacts a nostril of the individual.

Aspect 14. The method of aspect 7, comprising the step of removing the device from an envelope, wherein said step is carried out after step (a).

Aspect 15. The method of aspect 7, wherein an individual who carries out step (b) is a different individual than the individual in need of the naloxone.

Aspect 16. The method of aspect 7, wherein step (c) is carried out a single time, and wherein carrying out step (c) the single time results in release of at least 4 mg of naloxone onto the nasal mucosa of the individual.

Aspect 17. The method of aspect 7, wherein step (c) results in release of at least 80% of the volume of the liquid composition containing naloxone from the applicator.

Aspect 1A. A device for delivering naloxone to a patient, wherein the device comprises: a handle comprising a proximate end and a distal end; and a nasal stop attached to the handle toward the distal end; an applicator coupled to the distal end, wherein the applicator comprises a foam, wherein the distance between the nasal stop and the distal end of the applicator is from 15 mm to 31 mm.

Aspect 2A. The device of aspect 1A, wherein the nasal stop and the applicator are configured to position the applicator proximate to the middle turbinate and the inferior turbinate when the applicator is inserted into the nasal cavity.

Aspect 3A. The device of any one of aspects 1A to 2A, wherein the nasal stop and the applicator are configured to such that when inserted into a nasal cavity distal end of the applicator is situated from 1.5 cm to 3.0 cm from the nasal opening.

Aspect 4A. The device of any one of aspects 1A to 3A, wherein the applicator has a diameter from 6 mm to 12 mm and a length from 12 mm to 30 mm.

Aspect 5A. The device of any one of aspects 1A to 4A, wherein the applicator has a volume from 0.055 in$^3$ to 0.075 in$^3$.

Aspect 6A. The device of any one of aspects 1A to 5A, wherein the foam comprises a reticulated foam.

Aspect 7A. The device of any one of aspects 1A to 6A, wherein the foam comprises a polyurethane foam.

Aspect 8A. The device of any one of aspects 1A to 7A, wherein the foam is characterized by a pore size from 80 ppi to 100 ppi as determined by the pressure drop, a density from 1.70 lb/ft3 to 2.50 lb/ft$^3$.

Aspect 9A. The device of any one of aspects 1A to 8A, wherein the foam is characterized by a compression force deflection (CFD) at 25% R (2 m×2 m×1 m) greater than 0.4 psi.

Aspect 10A. The device of any one of aspects 1A to 9A, wherein the foam is characterized by a compression set at 50% deflection of less than 10%.

Aspect 11A. The device of any one of aspects 1A to 10A, wherein the foam is characterized by a compression set at 50% deflection of greater than 10%.

Aspect 12A. The device of any one of aspects 1A to 11A, wherein the foam is a crushable foam.

Aspect 13A. The device of any one of aspects 1A to 12A, wherein the foam is characterized by a dose proportional release of naloxone hydrochloride for a 60 mg/mL naloxone composition.

Aspect 14A. The device of any one of aspects 1A to 13A, wherein the foam is characterized by a release of naloxone HCl with a relative standard deviation (RSD of less than 6%.

Aspect 15A. The device of any one of aspects 1A to 14A, wherein the foam comprises from 70 µL to 350 µL of a naloxone composition.

Aspect 16A. The device of aspect 15A, wherein the naloxone composition comprises from 1 mg to 20 mg of naloxone hydrochloride.

Aspect 17A. The device of any one of aspects 15A to 16A, wherein the naloxone composition comprises a naloxone concentration from 20 mg/mL to 80 mg/mL.

Aspect 18A. The device of any one of aspects 15A to 17A, wherein the naloxone composition comprises a stabilizing agent, a tonicity agent, a chelating agent, and a preservative.

Aspect 19A. The device of any one of aspects 15A to 18A, wherein the composition comprises water, naloxone, citric acid, ethylenediaminetetraacetic acid, benzalkonium chloride, and sodium chloride.

Aspect 20A. The device of any one of aspects 15A to 19A, wherein the composition has a viscosity 0.1 centipoise to 10 centipoise at 20° C.

Aspect 21A. The device of any one of aspects 15A to 20A, wherein the composition has a pH from 3.5 to 5.5.

Aspect 22A. The device of any one of aspects 15A to 21A, wherein the composition consists of water, naloxone, citric acid, ethylenediamine tetra acetic acid, benzalkonium chloride, and sodium chloride.

Aspect 23A. The device of any one of aspects 1A to 22A, wherein the device comprises a cap disposed over the applicator.

Aspect 24A. A package comprising the device of any one of aspects 1A to 23A enclosed within a package.

Aspect 25A. A kit comprising the package of aspect 24A, and instructions for using the device.

Aspect 26A. A method for treating an opioid overdose in a patient, comprising: (a) inserting the applicator of the device any one of aspects 15A to 22A into the nasal cavity of a nostril of a patient having an opioid overdose; (b) bringing the stop into contact with the anterior naris to situate the applicator in proximity to the middle turbinate and the inferior turbinate; and (c) squeezing the nostril against the applicator for from 1 seconds to 5 seconds to release the naloxone hydrochloride composition from the applicator and to administer the naloxone hydrochloride composition to the nasal mucosa, to thereby treat the opioid overdose.

Aspect 27A. The method of aspect 26A, wherein inserting, bringing, and squeezing are performed by a person other than the patient having the opioid overdose.

Aspect 28A. The method of any one of aspects 26A to 27A, wherein inserting the applicator comprises contacting the nasal mucosa between from 15 mm to 31 mm for the anterior naris.

Aspect 29A. The method of any one of aspects 26A to 28A, wherein, after squeezing the nostril, releasing the nostril and removing the applicator from the nostril.

Aspect 30A. The method of any one of aspects 26A to 29A, wherein, while squeezing the nostril, removing the applicator from the nostril.

Aspect 31A. The method of any one of aspects 26A to 30A, wherein the method comprises, repeating steps (a), (b), and (c) using a new device on the same nostril of the patient Aspect 32A. The method of any one of aspects 26A to 31A, wherein the method comprises, repeating steps (a), (b), and (c) using a new device on a different nostril of the patient.

Aspect 33A. The method of any one of aspects 26A to 32A, wherein squeezing the nostril results in greater than 30 vol % of the naloxone hydrochloride composition initially retained by the applicator being released from the applicator.

Aspect 34A. The method of any one of aspects 26A to 33A, wherein squeezing the nostril results in greater than 30 wt % of the naloxone hydrochloride composition initially retained by the applicator being released from the applicator.

Aspect 35A. The method of any one of aspects 26A to 34A, wherein the method results in from 4 mg to 20 mg of naloxone hydrochloride being released from the applicator.

Aspect 36A. The method of any one of aspects 26A to 35A, wherein following administration to a population of patients the method provides a naloxone plasma pharmacokinetic profile characterized by, $T_{max}$ from 0.23 h to 0.29 h;

a $C_{max}$ from 5,129 pg/mL to 6,288 pg/mL; a $pAUC_{30}$ from 400 pg×h/mL to 489 400 pg×h/mL; an $AUC_{last}$ from 7,192 400 pg×h/mL to 8,791 pg×h/mL; and a $T_{1/2}$ from 2.1 h to 2.8 h, wherein the applicator initially retains 8 mg of naloxone HCl in a composition comprising 60 mg/mL naloxone hydrochloride.

Aspect 37A. The method of any one of aspects 26A to 36A, wherein following administration to a population of patients the method provides a naloxone plasma pharmacokinetic profile that is bioequivalent to the pharmacokinetic profile for Treatment 3A shown in FIGS. 9 and 10, wherein the applicator initially retains 12 mg of naloxone HCl in a composition comprising 60 mg/mL naloxone hydrochloride.

Aspect 38A. The method of any one of aspects 26A to 37A, wherein following administration to a population of patients the method provides a naloxone plasma pharmacokinetic profile characterized by $T_{max}$ less than 0.3 (±10%) hour and a $C_{max}$ from 4,400 (±10%) pg/mL to 6,600 (±10%) pg/mL, wherein the applicator initially retains 12 mg of naloxone HCl in a composition comprising 60 mg/mL naloxone hydrochloride.

Aspect 39A. The method of any one of aspects 26A to 38A, wherein, following administration of from 4.0 mg to 5.0 mg of naloxone hydrochloride to a population of patients, the naloxone plasma pharmacokinetic profile is bioequivalent to a pharmacokinetic profile characterized by a $C_{max}$ of 5,700 (±10%) pg/mL, a $T_{max}$ (±10%) of 0.26 hours, and a $AUC_{last}$ of 8,000 (±10%) pg×hr/mL wherein the applicator initially retains 12 mg of naloxone HCl in a composition comprising 60 mg/mL naloxone hydrochloride.

Aspect 40A. The method of any one of aspects 26A to 39A, wherein following administration of from 4.0 mg to 5.0 mg of naloxone hydrochloride to a population of patients, the naloxone plasma pharmacokinetic profile is further characterized by a pAUC at 5 min of 446 (±10%) pg×hr/mL, and a pAUC at 15 min of 834 (±10%) pg×hr/mL wherein the applicator initially retains 12 mg of naloxone HCl in a composition comprising 60 mg/mL naloxone hydrochloride.

Aspect 41A. The method of any one of aspects 26A to 40A, wherein following administration of from 4.0 mg to 5.0 mg of naloxone to a population of patients, the naloxone plasma pharmacokinetic profile is characterized by a $T_{1/2}$ of 2.3 (±10%) hours.

Aspect 42A. The method of any one of aspects 26A to 41A, wherein following administration of from 4.0 mg to 5.0 mg of naloxone to a population of patients, the naloxone plasma pharmacokinetic profile is characterized by a pAUC at 30 min of 3,511 (+10%) pg×hr/mL.

Aspect 43A. The method of any one of aspects 26A to 42A, wherein the opioid overdose is caused by buprenorphine, carfentanil, codeine, fentanyl, hydrocodone, hydromorphone, meperidine, methadone, morphine, opium, oxycodone, oxymorphone, tramadol, or a combination of any of the foregoing.

Aspect 44A. The method of any one of aspects 26A to 43A, wherein a single dose of 4 mg naloxone hydrochloride administered using a device and method provided by the present disclosure, when administered to a population of patients exhibits a $T_{max}$ from 0.23 h to 0.29 h; a $C_{max}$ from 5,129 pg/mL to 6,288 pg/mL; a $pAUC_{30}$ from 400 pg×h/mL to 489 pg×h/mL; an $AUC_{last}$ from 7,192 pg×h/mL to 8,791 pg×h/mL; and a $T_{1/2}$ from 2.1 h to 2.8 h.

Aspect 45A. The method of any one of aspects 26A to 44A, wherein a single dose of 4 mg naloxone hydrochloride administered using a device and method provided by the present disclosure, when administered to a population of patients exhibits a $T_{max}$ from 0.24 h to 0.28 h; a $C_{max}$ from 5,414 pg/mL to 5,983 pg/mL; a $pAUC_{30}$ from 423 pg×h/mL to 467 pg×h/mL; an $AUC_{last}$ from 7,552 pg×h/mL to 8,391 pg×h/mL; and/or a $T_{1/2}$ from 2.2 h to 2.5 h.

EXAMPLES

The following examples describe in detail devices provided by the present disclosure, properties of devices provided by the present disclosure, and methods of using devices provided by the present disclosure. It will be apparent to those skilled in the art that many modifications, both to materials and methods, may be practiced without departing from the scope of the disclosure.

Example 1

Naloxone Formulation

The naloxone compositions used in the examples had a concentration of naloxone hydrochloride from 20 mg/mL to 60 mg/mL provided as the appropriate weight of naloxone HCl dihydrate, 0.05 wt % Na2EDTA, 0.10 wt % BKC, 0.15 wt % NaCl, and 10 mM citric acid. The pH of the naloxone compositions was adjusted to 4.5 with NaOH or HCl.

Example 2

Device

The devices used in the examples had the dimensions as shown in FIGS. 12A and 12B. The handle and stop were made from polypropylene. The applicator was a reticulated polyurethane foam having the following properties: 80 ppi to 100 ppi pore size (pressure drop); density from 1.90 lb/ft$^3$ to 2.30 lb/ft$^3$ (30 kg/m$^3$ to 37 kg/m$^3$); tensile strength greater than 21 psi (145 kPa); elongation greater than 225%; tear strength greater than 2.5 lb/in (350 N/m); CFD 25% R (2 in×2 in×1 in) greater than 0.4 psi (2.7 kpPa); CFD 65% R (2 in×2 in×1 in) 0.55 psi (3.1 kPa); and compression set 50% deflection less than 10%

Example 3

Applicator Dose Linearity

The ability of applicator materials to release a pharmaceutical composition was evaluated using an absorbent material test method. Applicators were loaded with a known volume of a pharmaceutical composition. The applicators retaining a known volume of a naloxone composition were rolled 4 times over a 2.5×10 cm$^2$ strip of Benchkote® Plus absorbent paper. The paper is highly absorbent on one side and has a thin polyethylene coating on the other, effectively preventing liquid from seeping through the paper. The sum of the loaded naloxone hydrochloride dose, the delivered dose, and the residual amount in swab was determined through gravimetric means and delivered mass balance.

Figure 4:
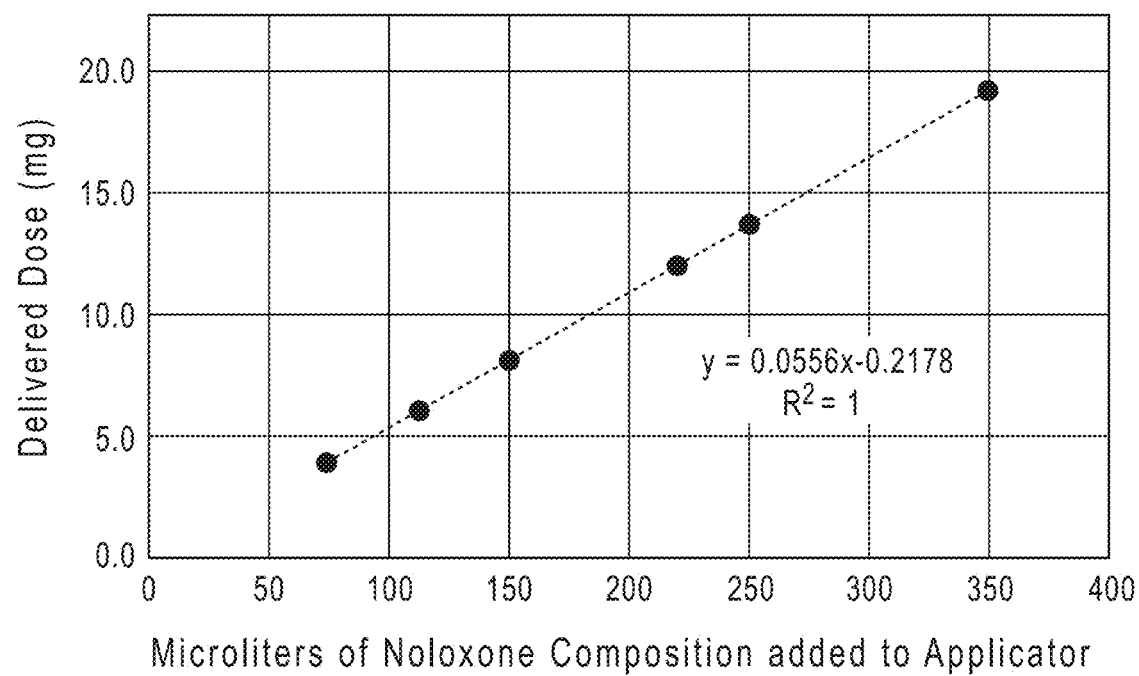
FIG. 4 shows ex vivo dose delivery results for delivery of naloxone hydrochloride using a device provided by the present disclosure.

FIG. 4 shows ex vivo results of delivery of naloxone HCl by a reticulated polyurethane foam applicator as described in Example 3 and using different initial volumes of the naloxone composition described in Example 1. More specifically, FIG. 4 shows the amount in mg of naloxone released by the applicator on the Y-axis and the volume in μL of a naloxone composition having a naloxone HCl concentration 60 mg/mL initially retained by the applicator on the X-axis.

The results were obtained using the technique described above for measuring release of a compound from the applicator, wherein the trial of the device was repeated for each composition amount. That is, every point on the graph represents a different trial of an applicator using the shown composition amounts. It is notable that the release profile of the device with increasing volume of the naloxone composition held by the applicator remained linear. That is, the amount released remained consistent in a linear fashion as the amount of the composition held by the applicator was increased. This means that using the device described herein, any specific dosage of a compound can be delivered based on the amount of composition that is initially held by a polyurethane foam applicator. For example, as shown on the graph, approximately 90 µL of the naloxone composition held by the applicator resulted in release of 5 gm of naloxone HCl. For example, 350 µL of the naloxone composition resulted in delivery of approximately 19 mg of naloxone HCl released. Each data point on the graph includes error bars which correspond to the % RSD (relative standard deviation) of 2.6, 3.6, 1.7, 2.0, 2.7 and 1.9 respectively.

The in vitro assay indicates that the delivered naloxone HCl dose can be adjusted by adjusting the volume of the applied naloxone composition. For example, the volume required to cover the in vitro released dose range of 4 mg to 12 mg naloxone HCl is from 77.0 µL to 220.0 µL.

Example 4

Comparison of Applicator Materials

The ability of different applicator materials to release a pharmaceutical composition was determined.

Table 1 shows data collected from 10 different applicators comprising cotton. Each of the 10 applicators comprising cotton was placed in a vial with a naloxone containing composition (where the vial contained the same fixed volume for each of the applicators for which data was collected) so that each applicator absorbed the same volume of the naloxone containing composition. Then, each applicator was contacted against an absorbent paper surface by rolling the applicator 4 times across the surface of the absorbent paper (Benchkote® Plus). The quantity of the naloxone composition held by an applicator was measured before the applicator contacted the absorbent paper surface. The quantity of the naloxone formulation transferred to the absorbent paper was measured.

Table 1 shows the percent amount of the naloxone composition remaining on each one of the 10 cotton applicators after each applicator contacted the paper surface.

TABLE 1

| Cotton applicator. | |
|---|---|
| Applicator No. | Delivered (%) |
| 1 | 37.5 |
| 2 | 39.3 |
| 3 | 38.0 |
| 4 | 37.2 |
| 5 | 24.6 |
| 6 | 42.5 |
| 7 | 49.4 |
| 8 | 28.3 |
| 9 | 28.7 |
| 10 | 27.2 |
| Average | 35.3 |
| SD | 7.8 |
| % RSD | 22.1 |

Table 2 shows data collected from 10 different applicators comprising a polyurethane foam. Each of the 10 applicators was placed in a vial of a naloxone composition (where the vial contained the same fixed volume for each of the applicators for which data was collected) so that each applicator adsorbed a quantity of the naloxone composition. Then, each applicator was contacted against an absorbent paper so that an amount of the naloxone composition was transferred from the applicator to the absorbent paper. The quantity of the naloxone composition held by an applicator was measured before and after the applicator contacted the absorbent paper.

Table 2 shows the percent amount of the naloxone composition remaining on each one of the 10 applicators after each applicator contacted the paper surface. Table 2 also shows the percent amount of the naloxone composition transferred to the absorbent paper surface.

TABLE 2

| Polyurethane foam applicator. | |
|---|---|
| Applicator No. | Delivered (%) |
| 1 | 88.4 |
| 2 | 92.2 |
| 3 | 91.4 |
| 4 | 90.5 |
| 5 | 91.3 |
| 6 | 94.3 |
| 7 | 92.7 |
| 8 | 91.4 |
| 9 | 91.8 |
| 10 | 92.3 |
| Average | 91.6 |
| SD | 1.5 |
| % RSD | 1.6 |

Comparing the data presented in Table 1 and Table 2, the applicator comprising polyurethane foam performed substantially better than the applicator comprising cotton. The average delivered naloxone composition was 91.6% for the polyurethane foam applicator as compared to 35.3% delivered by the cotton applicator. The standard deviation in the group of polyurethane foam applicators was 1.5% corresponding to a relative standard deviation of 1.6% compared to a standard deviation of 7.8% and a relative standard deviation of 22.1% for the cotton applicators.

Example 5

Stability of Naloxone Composition

Naloxone compositions were prepared as described in Example 1.

The stability of high concentration standalone naloxone compositions of naloxone (60 mg/mL) were assessed under three conditions. The conditions under which the samples were stored for stability analysis were: (i) 2° C. to 8° C.; (ii) 40° C.; and (iii) 60° C.

Immediately after preparation, both compositions were clear and colorless, and the pH was 4.5 for both compositions. The naloxone hydrochloride concentration for Composition 1 wt 60 mg/mL and for Composition 2 was 50 mg/mL. The osmolality of all samples for both strengths was in the range from 293 mOsmol/kg to 304 mOsmol/kg. Samples stored at 2° C. to 8° C. and at 40° C. remained colorless and clear. Both compositions stored at 60° C. changed color to a light yellow but clear solution.

With respect to pH, all naloxone compositions stored at 2° C. to 8° C. and at 40° C. were unchanged (within 0.1 pH unit of the initial composition pH). Naloxone compositions stored at 60° C. decreased in pH by approx. 0.3 to 0.4 pH units, possibly indicating degradation of the naloxone or excipients. Additionally, it is evident that the samples stored at 60° C. underwent some degradation as shown by a slightly reduced recovery and purity, as shown in Table 3. All compositions stored at 2° C. to 8° C. and at 40° C. had insignificant changes in purity and recovery.

TABLE 3

Stability of naloxone compositions

| Composition | Storage Conditions | Initial ($t_0$) Osmolality mOsmol/kg | Initial ($t_0$) pH | Initial ($t_0$) Naloxone HCl Conc. mg/mL | 1 Month pH | 1 Month Recovery % of Initial | 1 Month Purity (%) |
|---|---|---|---|---|---|---|---|
| 1 | 2° C. to 8° C. | 304 | 4.5 | 57.4 | 4.4 | 99.4 | 99.5 |
|   | 40° C. |  |  |  | 4.5 | 102.1 | 99.7 |
|   | 60° C. |  |  |  | 4.1 | 96.4 | 97.5 |
| 2 | 2° C. to 8° C. | 295 | 4.5 | 57.5 | 4.4 | 100.5 | 99.9 |
|   | 40° C. |  |  |  | 4.5 | 100.9 | 99.7 |
|   | 60° C. |  |  |  | 4.1 | 93.7 | 98.1 |

The high concentration compositions (60 mg/mL) were stored and assessed longer-term at (i) 2° C. to 8° C.; and at (ii) 40° C./75% RH. The results are presented in Tables 4-7. Purity was determined using HPLC-UV analysis for the measurement of six naloxone degradation products.

TABLE 4

Long term stability of 60 mg/mL naloxone composition at 4° C.

| Test | Initial | 1 Month | 2 Moth | 3 Month | 4 Month |
|---|---|---|---|---|---|
| Appearance | Clear and colorless solution | Clear and colorless solution | Clear and colorless solution | Clear and colorless solution | Clear and colorless solution |
| Naloxone HCl Concentration (mg/mL) | 57.8 | 57.5 | 56.5 | 55.8 | 55.5 |
| Purity (%) | 99.9 | 99.9 | 99.9 | 99.8 | 99.9 |
| pH | 4.52 | 4.43 | 4.40 | 4.43 | 4.48 |

TABLE 5

Long term stability of 60 mg/mL naloxone composition at 40° C./75% RH

| Test | Initial | 1 Month | 2 Moth | 3 Month | 4 Month |
|---|---|---|---|---|---|
| Appearance | Clear and colorless solution | Clear and colorless solution | Clear and colorless solution | Clear solution with slight yellow brown tinge | Clear solution with slight yellow brown tinge |
| Naloxone HCl Concentration (mg/mL) | 57.8 | 59.0 | 56.5 | 55.7 | 55.8 |
| Purity (%) | 99.9 | 99.7 | 99.3 | 99.1 | 99.0 |
| pH | 4.52 | 4.46 | 4.36 | 4.31 | 4.24 |

TABLE 6

Long term stability of 60 mg/mL naloxone composition without $Na_2EDTA$ at 40° C./75% RH.

| Test | Initial | 1 Month | 2 Moth | 3 Month | 4 Month |
|---|---|---|---|---|---|
| Appearance | Clear and colorless solution | Clear and colorless solution | Clear and colorless solution | Clear solution with slight yellow brown tinge | Clear solution with slight yellow brown tinge |
| Naloxone HCl Concentration (mg/mL) | 57.5 | 58.1 | 55.8 | 55.8 | 55.4 |
| Purity (%) | 99.9 | 99.7 | 99.3 | 99.1 | 99.0 |
| pH | 4.51 | 4.44 | 4.33 | 4.26 | 4.25 |

TABLE 7

Long term stability of 60 mg/mL naloxone composition without $Na_2EDTA$ at 4° C.

| Test | Initial | 1 Month | 2 Moth | 3 Month | 4 Month |
|---|---|---|---|---|---|
| Appearance | Clear and colorless solution | Clear and colorless solution | Clear and colorless solution | Clear and colorless solution | Clear and colorless solution |
| Naloxone HCl Concentration (mg/mL) | 57.5 | 57.8 | 55.8 | 55.9 | 56.5 |
| Purity (%) | 99.9 | 99.9 | 99.9 | 99.8 | 99.8 |
| pH | 4.51 | 4.46 | 4.39 | 4.37 | 4.50 |

Drug/device combinations with high concentration compositions of naloxone hydrochloride (60 mg/mL) were stored at 25° C. and at 40° C. The results are shown in Tables 8 and 9.

TABLE 8

Long term purity stability of 60 mg/mL naloxone composition loaded on the applicator at 25° C./60% RH.

| 25° C./60% RH | Initial | 1 Week | 2 Week | 3 Week | 3 Month | 6 Month |
|---|---|---|---|---|---|---|
| 12 mg dose | 99.9 | 99.9 | 99.9 | 99.9 | 99.6 | 99.6 |
| 6 mg dose | 99.9 | 99.9 | 99.9 | 99.9 | 99.6 | 99.6 |
| 4 mg dose | 99.9 | 99.9 | 99.9 | 99.9 | 99.6 | 99.7 |

TABLE 9

Long term purity stability of 60 mg/mL naloxone composition loaded on the applicator at 40° C./75% RH.

| 40° C./75% RH | Initial | 1 Week | 2 Week | 1 Month | 3 Month |
|---|---|---|---|---|---|
| 12 mg dose | 99.9 | 99.9 | 99.8 | 99.6 | 99.0 |
| 6 mg dose | 99.9 | 99.9 | 99.8 | 99.7 | 99.1 |
| 4 mg dose | 99.8 | 99.9 | 99.9 | 99.8 | 99.8 |

The observed purity for the drug/device combination at room temperature remained over 99.5%.

Example 6

Naloxone Plasma Pharmacokinetics (1)

The plasma naloxone PK profiles in 10 healthy human subjects was measured following administration of naloxone compositions having different naloxone HCl concentrations. The naloxone compositions were prepared as described in Example 1 and the device used to intranasally administer the naloxone compositions is described in Example 2 and included a reticulated polyurethane foam applicator.

To deliver the naloxone composition, the applicator was inserted into the nasal passage until the stop rested against the anterior naris such at that the applicator contacted the nasal mucosa in proximity to the tip of the middle turbinate and the tip of inferior turbinate with the applicator causing release of the naloxone composition onto the nasal mucosa. The applicator holding the naloxone composition was pressed and swirled three times against the nasal mucosa of the subject. The results are presented in FIGS. 5-7.

Figure 5:
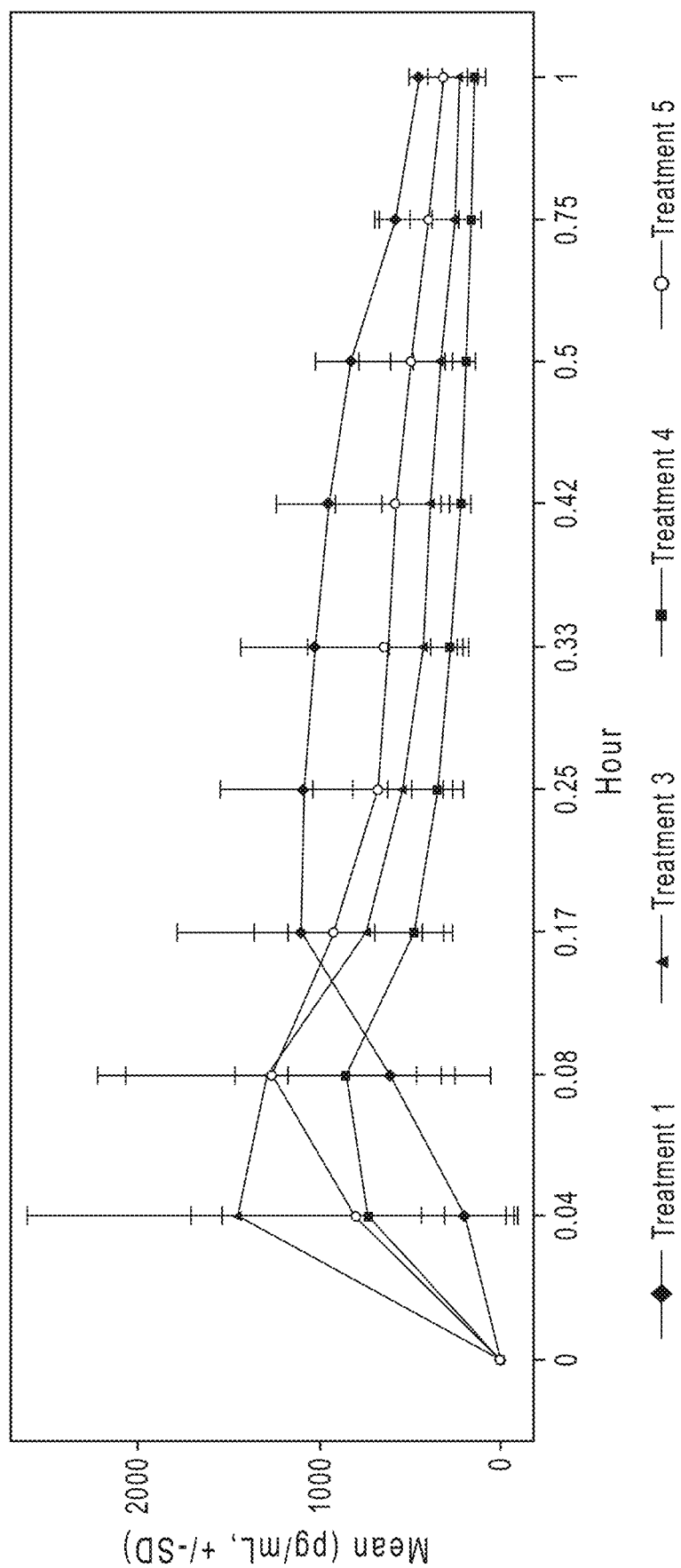
FIG. 5 shows the plasma naloxone pharmacokinetic (PK) profile collected from 10 human subjects following administration of naloxone hydrochloride using different methods and/or doses.

FIG. 5 shows PK profiles collected from 10 human subjects to whom a naloxone composition was administered using different techniques and compositions. FIG. 5 shows mean plasma naloxone concentration-time profiles for all 10 human subjects to whom naloxone compositions were administered. Data in the graph is expressed as a mean with the SD shown by the bars. The treatment conditions are summarized in Table 10.

TABLE 10

Treatment conditions.

| Treatment | Method | Dose Naloxone HCl (mg) | Number of Doses |
|---|---|---|---|
| Treatment 1 | Intramuscular Injection | 0.4 | 1 |
| Treatment 2 | Narcan ® nasal spray | 4 | 1 |
| Treatment 3 | Nasal Applicator | 8 | 1 |
| Treatment 4 | Nasal Applicator | 4 | 1 |
| Treatment 5 | Nasal Applicator | 12 | 1 |

Figure 6:
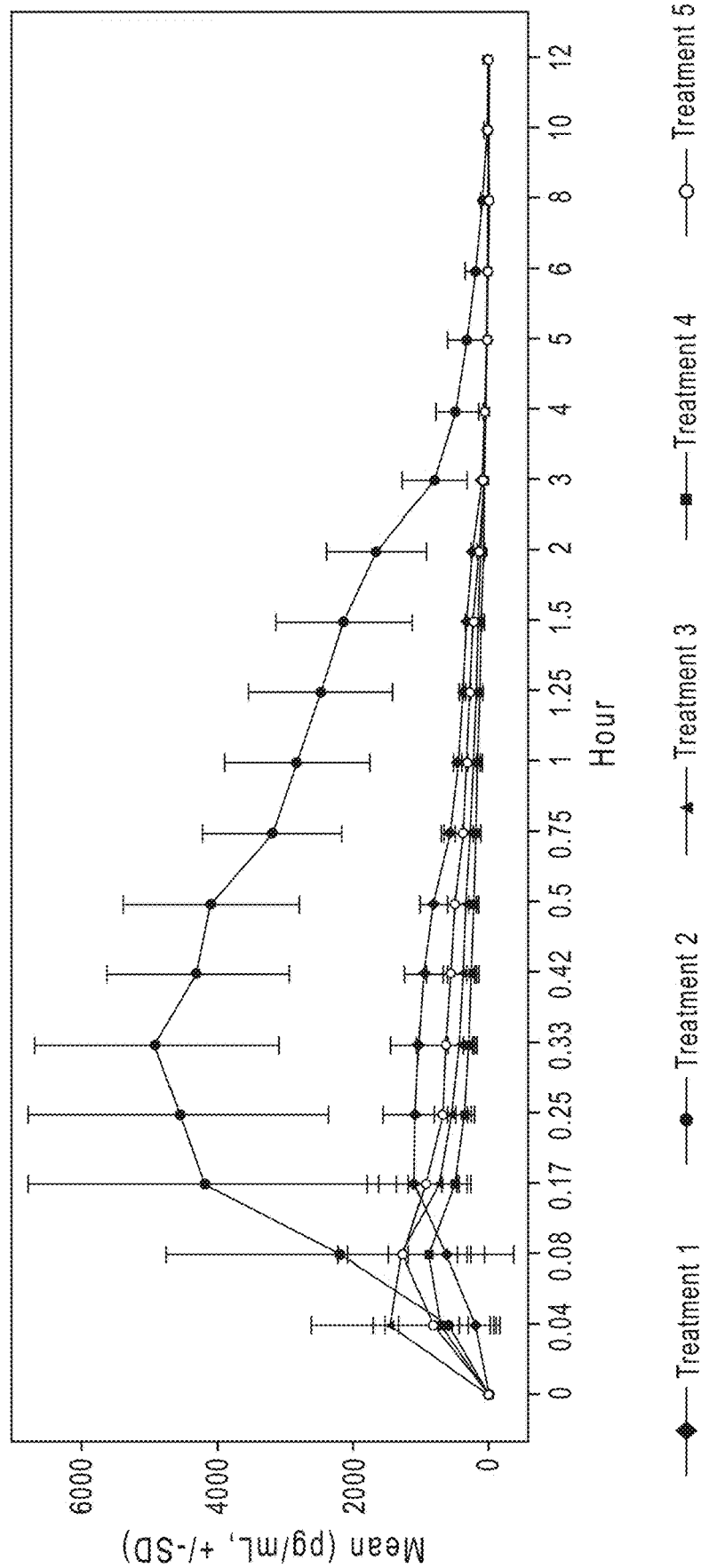
FIG. 6 shows the graph of FIG. 5 with the addition of data for an additional treatment modality labeled Treatment 2. For Treatment 2 naloxone hydrochloride was administered by means of a single nasal spray containing 4 mg of naloxone hydrochloride.

FIG. 6 shows the graph of FIG. 5 with the addition of data for an additional treatment modality labeled Treatment 2. In Treatment 2 a single Narcan® nasal spray of a composition containing 4 mg of naloxone HCl was administered. Narcan® nasal spray is supplied as a single dose intranasal spray containing 2 mg or 4 mg of naloxone hydrochloride in a volume of 0.1 mL.

The residual naloxone that remained on the applicators in Treatment 3, Treatment 4, and Treatment 5 after administration was about 80%.

Notwithstanding the relatively high residual amount of naloxone HCl that remained on the applicator, as shown in FIGS. 5 and 6, Treatment 3, Treatment 4, and Treatment 5 out-performed the IM injection and nasal spray in terms of the short $T_{max}$. For example, for Treatment 3, $T_{max}$ was achieved in about 4.5 min as compared to about 30 min using the nasal spray. While the method of administration resulted in only release of about 20% of the naloxone composition held on the applicator being released, the focal release onto the respiratory epithelium in the vicinity of the middle turbinate and the inferior turbinate in efficient transfer of the naloxone composition across the nasal mucosa and into the bloodstream of the subjects. This contrasts with a nasal spray that spreads the naloxone composition around the inside of the nasal passage without achieving a focal delivery of the naloxone composition to the respiratory epithelium.

FIG. 7 shows a table summarizing the PK parameters based on the PK profiles shown in FIGS. 5 and 6. As presented, FIG. 7 includes AUC (Area Under Curve) and partial AUC data for the different treatments. The first column of the table data shown in the rows corresponds to spray administration, IM administration, administration with a polyurethane foam applicator holding 8 mg of naloxone HCl, administration with a polyurethane foam applicator holding 4 mg of naloxone HCl, and administration with a polyurethane foam applicator holding 12 mg of naloxone HCl. As shown in FIG. 7, only about 20% of the naloxone HCl was released from the three polyurethane foam applicators. Partial AUC data was calculated at 2.4 minutes, 4.8 minutes, and 10 minutes for each of the five administrations that were tested (i.e. nasal spray, IM injection, polyurethane foam applicator at 8 mg, polyurethane foam applicator at 4 mg, and polyurethane foam applicator at 12 mg).

FIG. 8 shows a table with proposed administration techniques intended to reduce the amount of naloxone HCl remaining on an applicator after administration to the nasal mucosa.

Example 7

Naloxone Plasma Pharmacokinetics (2)

The plasma naloxone concentration following administration of naloxone using various methods was determined.

The plasma naloxone PK profiles in 10 healthy human subjects was measured following administration of naloxone compositions having different naloxone HCl concentrations. The naloxone compositions were prepared as described in Example 1 and the device used to intranasally administer the naloxone compositions is described in Example 2 and included a reticulated polyurethane foam applicator.

The treatment methods are provided in Table 11.

TABLE 11

Treatment conditions.

| Treatment | Method | Dose Naloxone HCl (mg) | Number of Doses |
|---|---|---|---|
| Treatment 1A | Intramuscular Injection | 0.4 | 1 |
| Treatment 2A | Narcan ® nasal spray | 4 | 1 |
| Treatment 3A | Nasal Applicator | 12 | 1 |
| Treatment 4A | Nasal Applicator | 12 | 2 |
| Treatment 5A | Nasal Applicator | 8 | 2 |

To administer the naloxone composition the applicator was inserted into the nasal cavity until the stop contacted the anterior naris. The nostrils were then firmly squeezed for 3 seconds between a finger and thumb. While maintaining pressure on the nostrils the applicator was gently removed from the nostril.

When administering two doses using the nasal applicator as in Treatment 4A, after the first dose of naloxone was administered using the first application, a second does was administered to the same nostril using a new device.

The plasma naloxone pharmacokinetic profiles obtained for 10 healthy human subjects for each treatment are shown in FIGS. 9 and 10, and the pharmacokinetic parameters are summarized in Table 12.

Table 13 shows the amount of the naloxone composition remaining on the applicator following administration.

TABLE 13

Naloxone composition on applicator following administration using a nasal applicator.

| Measurement | Treatment 3A Right Nostril | Treatment 4A Right Nostril | Treatment 4A Left Nostril | Treatment 5A Right Nostril | Treatment 5A Left Nostril |
|---|---|---|---|---|---|
| Average Naloxone HCl Retained (mg) | [1] 8.8 (1.6) | 9.1 (0.8) | 9.5 (0.8) | 6.8 (0.9) | 7.2 (0.4) |
| Average Naloxone HCl Released (mg) | 4.4 | 4.1 | 3.7 | 2.0 | 1.6 |
| Percent Naloxone HCl Released | 34 | 31 | 28 | 22 | 18 |

[1] Mean (standard deviation).

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. A nasal mucosal delivery device for use in treating an opioid overdose, comprising:
   a handle comprising a proximate end and a distal end;
   a nasal stop attached to the handle toward the distal end; and
   an applicator coupled to the distal end, wherein the applicator comprises a compressible polyurethane foam, wherein the compressible polyurethane foam:
      does not comprise microneedles;
      is characterized by its ability to hold and release a pre-determined dose of naloxone with a relative standard deviation of less than 6%;

TABLE 12

Plasma naloxone PK parameters following different administration methods.

| Treatment | Cmax (pg/mL) | pAUC (pg × hr/mL) | | | | | | AUC$_{last}$ (pg × hr/mL) | T$_{max}$ (hr) | T$_{1/2}$ (hr) |
|---|---|---|---|---|---|---|---|---|---|---|
| | | 2.5 min | 5 min | 10 min | 15 min | 1 hour | 3 hour | | | |
| Treatment 1A IM Injection 0.4 mg | 1,280 | 4 | 21 | 95 | 186 | 738 | 1,240 | 1,411 | 0.25 | 1.26 |
| Treatment 2A Narcan ® Nasal Spray 4 mg | 5,551 | 12 | 68 | 343 | 707 | 3,501 | 6,926 | 8,589 | 0.45 | 1.51 |
| Treatment 3A Nasal Applicator 12 mg One Dose | 5,699 | 31 | 125 | 446 | 834 | 3,511 | 6,525 | 7,993 | 0.26 | 2.34 |
| Treatment 4A Nasal Applicator 12 mg Two Doses | 8,078 | 44 | 164 | 579 | 1,100 | 4,741 | 8,803 | 10,998 | 0.29 | 3.40 |
| Treatment 5A Nasal Applicator 8 mg Two Doses | 4,822 | 51 | 188 | 549 | 854 | 2,736 | 4,818 | 6,135 | 0.22 | 2.66 | is configured to hold from 70 μL to 350 μL of a naloxone hydrochloride composition and to release a dose of the naloxone hydrochloride composition for treating an opioid overdose by squeezing a nostril against the compressible polyurethane foam, and contains from 1 mg to 20 mg of naloxone hydrochloride;

wherein the nasal stop is configured to rest against an anterior naris during use and to resist further penetration of the applicator into a nasal cavity; and wherein the distance between the nasal stop and the distal end of the applicator is from 15 mm to 30 mm.

2. The nasal mucosal delivery device of claim 1, wherein the naloxone hydrochloride composition comprises:
   a concentration of naloxone hydrochloride from 20 mg/mL to 60 mg/mL;
   0.05 wt % of disodium ethylenediaminetetraacetic acid;
   0.10 wt % of benzalkonium chloride;
   0.15 wt % of sodium chloride;
   10 nM citric acid; and
   a pH from 3.5 to 5.5.

3. The nasal mucosal delivery device of claim 1, wherein the compressible polyurethane foam is characterized by a dose proportional release of the naloxone hydrochloride composition.

4. The nasal mucosal delivery device of claim 1, wherein the compressible polyurethane foam has a volume from 500 mm³ to 1,500 mm³.

5. The nasal mucosal delivery device of claim 1, wherein the compressible polyurethane foam has a diameter from 6 mm to 12 mm and a length from 12 mm to 30 mm.

6. The nasal mucosal delivery device of claim 1, wherein the nasal stop has a diameter that is wider than an exterior of the nostril.

7. The nasal mucosal delivery device of claim 1, wherein squeezing comprises holding the nostril firmly closed against the compressible polyurethane foam for from 3 seconds to 6 seconds.

8. The nasal mucosal delivery device of claim 1, wherein squeezing comprises holding the nostril firmly closed against the compressible polyurethane foam for from 1 second to 5 seconds.

9. A method for treating an opioid overdose, comprising:
   (a) inserting the applicator of the nasal mucosal delivery device of claim 1 into a nasal cavity of a nostril of a patient having an opioid overdose, wherein the nostril comprises an anterior naris, a middle turbinate, an inferior turbinate, and a nasal mucosa;
   (b) bringing the nasal stop into contact with the anterior naris to situate the applicator in proximity to the middle turbinate and the inferior turbinate; and
   (c) squeezing the nostril against the compressible polyurethane foam to release the dose of the naloxone hydrochloride composition from the compressible polyurethane foam and to administer the naloxone hydrochloride composition to the nasal mucosa,
   to thereby treat the opioid overdose.

10. The method of claim 9, wherein inserting, bringing, and squeezing are performed by a person other than the patient having the opioid overdose.

11. The method of claim 9, wherein inserting the applicator comprises contacting the nasal mucosa between 15 mm to 30 mm from the anterior naris.

12. The method of claim 9, wherein, after squeezing the nostril, releasing the nostril and removing the applicator from the nostril.

13. The method of claim 9, wherein, while squeezing the nostril, removing the applicator from the nostril.

14. The method of claim 9, wherein following administration to a population of patients the method provides a plasma naloxone pharmacokinetic profile characterized by a $T_{max}$ less than 0.3 (+10%) hours.

* * * * *